United States Patent
Miyamoto et al.

(10) Patent No.: US 11,759,700 B2
(45) Date of Patent: Sep. 19, 2023

(54) COMPUTER-READABLE NON-TRANSITORY STORAGE MEDIUM HAVING GAME PROGRAM STORED THEREIN, GAME PROCESSING SYSTEM, GAME PROCESSING METHOD, AND GAME PROCESSING APPARATUS

(71) Applicant: NINTENDO CO., LTD., Kyoto (JP)

(72) Inventors: Shigeru Miyamoto, Kyoto (JP); Motoki Yano, Kyoto (JP); Keita Tsutsui, Tokyo (JP); Hiroki Asakawa, Tokyo (JP); Shohei Konno, Tokyo (JP)

(73) Assignee: Nintendo Co., Ltd., Kyoto (JP)

( * ) Notice: Subject to any disclaimer, the term of this patent is extended or adjusted under 35 U.S.C. 154(b) by 0 days.

(21) Appl. No.: 17/697,433

(22) Filed: Mar. 17, 2022

(65) Prior Publication Data

US 2022/0296995 A1    Sep. 22, 2022

(30) Foreign Application Priority Data

Mar. 22, 2021   (JP) .................................. 2021-046934

(51) Int. Cl.
*A63F 13/212*   (2014.01)
*A61B 5/11*   (2006.01)
*A63F 13/57*   (2014.01)

(52) U.S. Cl.
CPC .......... *A63F 13/212* (2014.09); *A61B 5/1118* (2013.01); *A63F 13/57* (2014.09)

(58) Field of Classification Search
CPC .... A63F 13/212; A63F 13/57; A63F 13/2145; A63F 13/216; A63F 13/46; A63F 13/69; A63F 13/92; A63F 13/35; A61B 5/1118
See application file for complete search history.

(56) References Cited

U.S. PATENT DOCUMENTS

2012/0214595 A1    8/2012   Kawamoto et al.

FOREIGN PATENT DOCUMENTS

JP          2012-170674         9/2012

*Primary Examiner* — Kevin Y Kim
(74) *Attorney, Agent, or Firm* — Nixon & Vanderhye PC

(57) ABSTRACT

Only a first parameter associated with an active object is incremented in accordance with an exercise amount of a user. In accordance with the exercise amount of the user, a second parameter is incremented even when the first parameter has not reached an upper limit, and the second parameter is incremented also when the first parameter has reached the upper limit. An in-game reward according to the active object with which the first parameter is associated is given to the user when the first parameter has reached the upper limit.

20 Claims, 16 Drawing Sheets

FIG.3
(1) ACQUISITION SCREEN (PETAL USE OPERATION SCREEN)
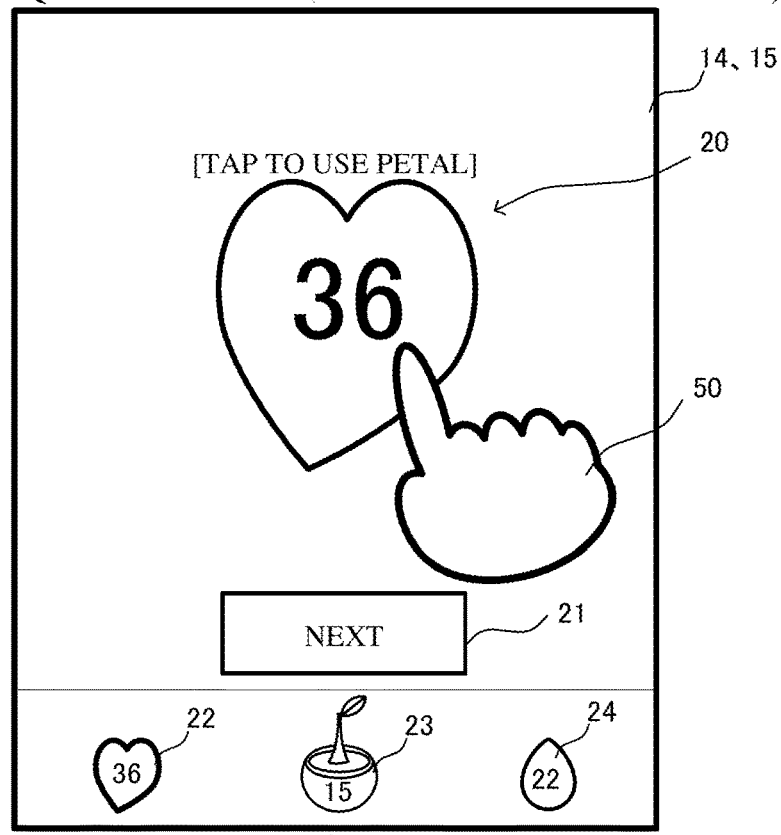
(2) ACQUISITION SCREEN (ACQUISITION NOTICE SCREEN)
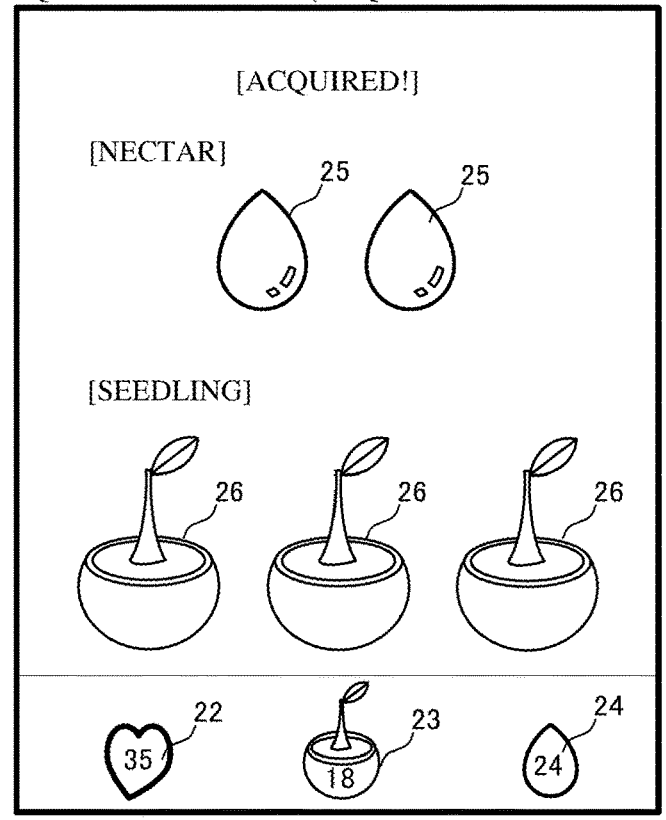

COMPUTER-READABLE NON-TRANSITORY STORAGE MEDIUM HAVING GAME PROGRAM STORED THEREIN, GAME PROCESSING SYSTEM, GAME PROCESSING METHOD, AND GAME PROCESSING APPARATUS

CROSS REFERENCE TO RELATED APPLICATION

This application claims priority to Japanese Patent Application No. 2021-46934 filed on Mar. 22, 2021, the entire contents of which are incorporated herein by reference.

FIELD

The exemplary embodiments relate to a game process in which game progress is changed in accordance with the exercise amount of a user.

BACKGROUND AND SUMMARY

Conventionally, there has been known a game in which coins are acquired in a game in accordance with the number of steps the user has walked, and growth of a game character can be promoted using the acquired coins.

In the above game, there is an upper limit on the number of coins that can be acquired during one day in accordance with the number of steps. Therefore, after the user has acquired coins to the upper limit, the user might be less motivated to walk (exercise).

Accordingly, an object of the exemplary embodiments is to provide a computer-readable non-transitory storage medium having a game program stored therein, and the like, that can keep motivation for a user to continue exercise.

Configuration examples for achieving the above objects will be shown below.

One configuration example is a non-transitory computer-readable storage medium having stored therein instructions that, when executed by a processor of an information processing apparatus, cause the information processing apparatus to perform operations including: associating a first parameter with each of a plurality of in-game objects independently; setting the in-game object the number of which is not more than an active upper limit number among the plurality of in-game objects, as an active object; incrementing only the first parameter associated with the active object, in accordance with an exercise amount of a user; in accordance with the exercise amount of the user, incrementing a second parameter even when the first parameter has not reached an upper limit, and incrementing the second parameter also when the first parameter has reached the upper limit; and incrementing the first parameter on the basis of decrementing the second parameter; and giving the user an in-game reward according to the active object with which the first parameter is associated, when the first parameter has reached the upper limit.

According to the above configuration example, also after the first parameter has reached the upper limit, the second parameter for refilling the first parameter is incremented in accordance with the exercise amount. Thus, also after the first parameter has reached the upper limit, the user can keep motivated to continue exercise. In addition, according to the above configuration example, there is an upper limit on the number of in-game objects (active objects) for which the first parameter is incremented in accordance with the exercise amount. Therefore, in a case where the user has more in-game objects than the upper limit number, it is possible to urge the user to repeatedly perform exercise.

In another configuration example, an amount by which the second parameter is incremented in accordance with the exercise amount of the user may not be made different between a case where the first parameter has reached the upper limit and a case where the first parameter has not reached the upper limit.

According to the above configuration example, it is possible to avoid such a configuration that the method for incrementing the second parameter is complicated and hard to understand.

In another configuration example, amounts by which the first parameter and the second parameter are incremented in accordance with the exercise amount of the user may be made equal between the first parameter and the second parameter.

According to the above configuration example, it is possible to avoid such a configuration that the method for incrementing parameters (first parameter and second parameter) is complicated and hard to understand.

In another configuration example, in a case where there are a plurality of the active objects, an amount by which the first parameter associated with each of the plurality of active objects is incremented in accordance with the exercise amount of the user may not be changed depending on a number of the active objects.

According to the above configuration example, since the first parameters for the plurality of active objects are incremented by the same amount in accordance with the exercise amount of the user, it is possible to avoid such a configuration that the method for incrementing a parameter (first parameter) is complicated and hard to understand.

In another configuration example, an amount by which the first parameter associated with each of the active objects is incremented on the basis of decrementing the second parameter may not be changed depending on the number of the active objects.

According to the above configuration example, since the first parameters for the plurality of active objects are incremented by the same amount, it is possible to avoid such a configuration that the method for incrementing a parameter (first parameter) is complicated and hard to understand.

In another configuration example, in a case of decrementing the second parameter, the decrement may be performed by a natural number multiple of a decrement unit.

According to the above configuration example, it is possible to avoid such a configuration that the method for incrementing a parameter (second parameter) is complicated and hard to understand.

In another configuration example, the second parameter may not be incremented in a case where the second parameter has reached an upper limit, and every time the second parameter is decremented by the natural number multiple of the decrement unit, the upper limit of the second parameter may be lowered by an amount corresponding to the natural number.

According to the above configuration example, it is possible to urge the user to raise the upper limit of the second parameter.

In another configuration example, the first parameter may not be incremented in a case where the first parameter has reached the upper limit.

In another configuration example, until the first parameter associated with the active object reaches the upper limit, the active object may be prohibited from changing to the in-game object other than said active object.

BRIEF DESCRIPTION OF THE DRAWINGS

FIG. 3 shows a non-limiting example of a game screen;

DETAILED DESCRIPTION OF NON-LIMITING EXAMPLE EMBODIMENTS

Hereinafter, one exemplary embodiment will be described.

[Hardware Configuration of Information Processing Apparatus]

First, the configuration of an information processing apparatus according to the exemplary embodiment will be described. In the exemplary embodiment, an information processing apparatus 10 is assumed to be a smart device such as a smartphone or a tablet, a hand-held game apparatus, a portable laptop computer, or the like, for example. In the following description, an information processing apparatus (e.g., smartphone) having a display screen and a touch panel integrated with each other will be described as an example. Therefore, an input operation is mainly an input to the touch panel. However, in another exemplary embodiment, an input operation may be performed using a physical controller connected to the information processing apparatus wirelessly or via wire, or using an input device formed integrally with the information processing apparatus, for example.

Figure 1:
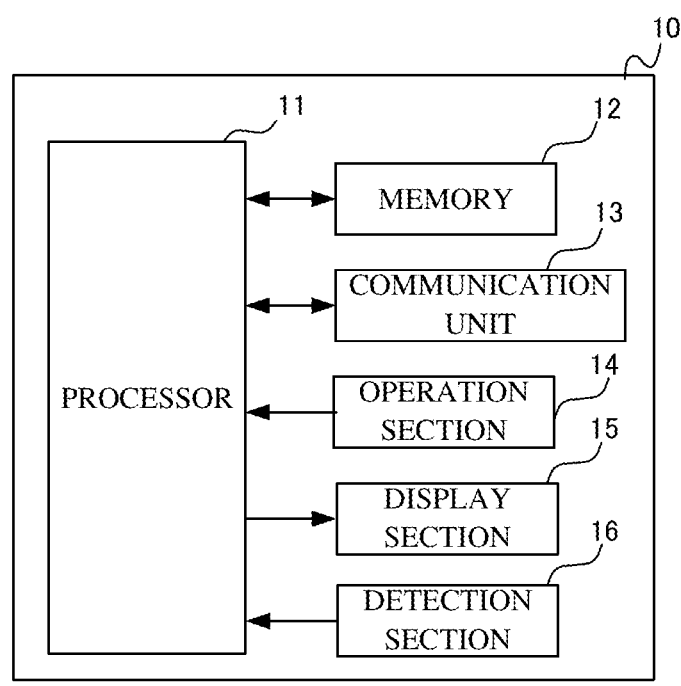
FIG. 1 is a block diagram showing a non-limiting example of an information processing apparatus 10.

FIG. 1 is a function block diagram of the information processing apparatus 10 according to the exemplary embodiment. In FIG. 1, the information processing apparatus 10 includes a processor 11, a memory 12, an operation section 14, a display section 15, and a detection section 16. The processor 11 executes information processing as described later and executes a system program (not shown) for controlling overall operation of the information processing apparatus 10, thereby controlling operation of the information processing apparatus 10. The processor 11 may be a single processor or may be formed from a plurality of processors. The memory 12 stores various programs to be executed by the processor 11 and various data to be used for the various programs. The memory 12 is a flash EEPROM or a hard disk device, for example. The operation section 14 is an input device for receiving an operation from a user, for example. The display section 15 is typically a liquid crystal display device. In the process according to the exemplary embodiment, a touch panel integrated with a liquid crystal screen is assumed as the operation section 14 and the display section 15. In another exemplary embodiment, a predetermined pointing device other than a touch panel may be used as the operation section 14. The detection section 16 is a device for detecting a walking (or running) action of the user carrying the information processing apparatus 10 (i.e., a device for detecting taken steps), and is, for example, an acceleration sensor.

[Outline of Game Process in Exemplary Embodiment]

Next, the outline of information processing executed in the exemplary embodiment will be described. In the exemplary embodiment, a game process for executing a game application (which may be referred to as "app") will be described as an example of the information processing. First, the outline of the game application (which may be simply referred to as "game") realized by the game process will be described. The game assumed in the exemplary embodiment is a game in which a game character (which may be referred to as "character" or "char") is acquired and the number of game characters is increased, by the user walking or running (which may be simply referred to as "walking").

More specifically, the game assumed in the exemplary embodiment is as follows. The user walks with the information processing apparatus 10 carried, to acquire a seedling or nectar. The user plants the acquired seedling in a planter, and then walks to grow the seedling. The user plucks the grown seedling as a character, and then walks, waits for time to pass, or feeds nectar to the character to grow the character and obtain (pick) a petal from the character. By using the acquired petal, the user can more readily acquire a seedling. Through repetition of such a cycle, the user enjoys walking (exercising) and increasing the number of characters. Hereinafter, with reference to the drawings, this game will be specifically described.

Figure 2:
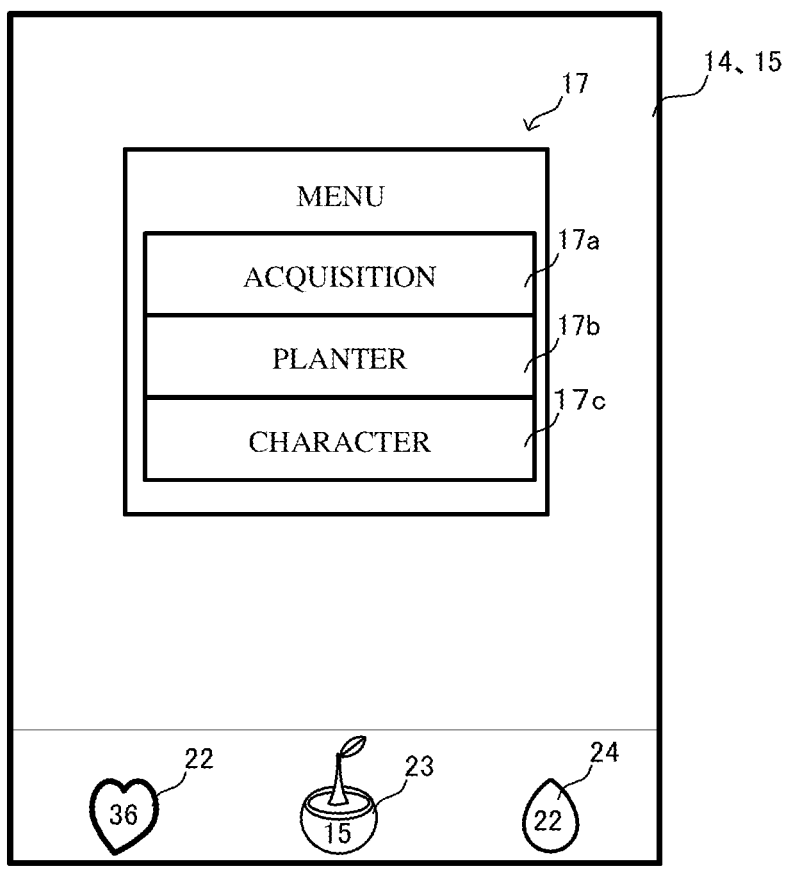
FIG. 2 shows a non-limiting example of a game screen.

FIG. 2 shows an example of a menu screen displayed when this game is started. As shown in FIG. 2, on the menu screen, a menu image 17 is displayed. The menu image 17 includes an acquisition menu image 17a, a planter menu image 17b, and a character menu image 17c as operation menus. When the user touches the acquisition menu image 17a, the screen shifts to an acquisition screen where the user can acquire a seedling or nectar as described later with reference to FIG. 3. When the user touches the planter menu image 17b, the screen shifts to a planter screen where the user can plant a seedling in a planter and grow the seedling into a character as described later with reference to FIG. 4, etc. When the user touches the character menu image 17c, the screen shifts to a character screen where the user can grow the character and obtain (pick) a petal from the character as described later with reference to FIG. 8, etc. As shown in FIG. 2, at the lower part of the menu screen, a petal count image 22 indicating the number of possessed petals, a seedling count image 23 indicating the number of possessed seedlings, and a nectar count image 24 indicating the number of possessed nectars, are displayed.

FIG. 3 shows an example of the acquisition screen. When the menu screen has shifted to the acquisition screen in accordance with a user's operation, as shown in FIG. 3(1), first, a petal use operation screen is displayed. On the petal use operation screen, a petal use image 20 including a petal image representing a comparatively large petal is displayed. In addition, a word image 21 on which a word "NEXT" is written, is displayed. In addition, as in the menu screen described in FIG. 2, at the lower part of the acquisition screen, the petal count image 22, the seedling count image 23, and the nectar count image 24 are displayed. On the petal use image 20, the number of possessed petals are displayed as in the petal count image 22.

As shown in FIG. 3(1), when the user taps the petal use image 20, in accordance with the number of times of the tap operation, the number of petals to be used is set and the displayed number of possessed petals is decremented. A hand 50 represents the user's hand operating the information processing apparatus 10. For example, in FIG. 3, when a tap operation is performed once, one (one petal) is set as the number of petals to be used, and the numbers of possessed petals displayed on the petal use image 20 and the petal count image 22 are decremented to 35. Then, when the word image 21 is tapped, the screen shifts to an acquisition notice screen shown in FIG. 3(2).

As shown in FIG. 3(2), on the acquisition notice screen, nectar images 25 and seedling images 26 are displayed, which are acquired by such a lottery that, the more the number of steps the user has walked with the information processing apparatus 10 carried is, the higher the winning probability is. In addition, in this lottery, the winning probability for a seedling increases as the number of used petals set by the user increases. In another exemplary embodiment, this lottery may be set such that the winning probabilities for both of a seedling and nectar increase as the number of used petals set by the user increases. In the example shown in FIG. 3(2), the user is notified that, as a result of the lottery in accordance with the number of steps of the user, two nectars are acquired with two nectar images 25 displayed, and three seedlings are acquired with three seedling images 26 displayed. In addition, along with this, the number on the nectar count image 24 is incremented by 2 to be 24, and the number on the seedling count image 23 is incremented by 3 to be 18.

Figure 4:
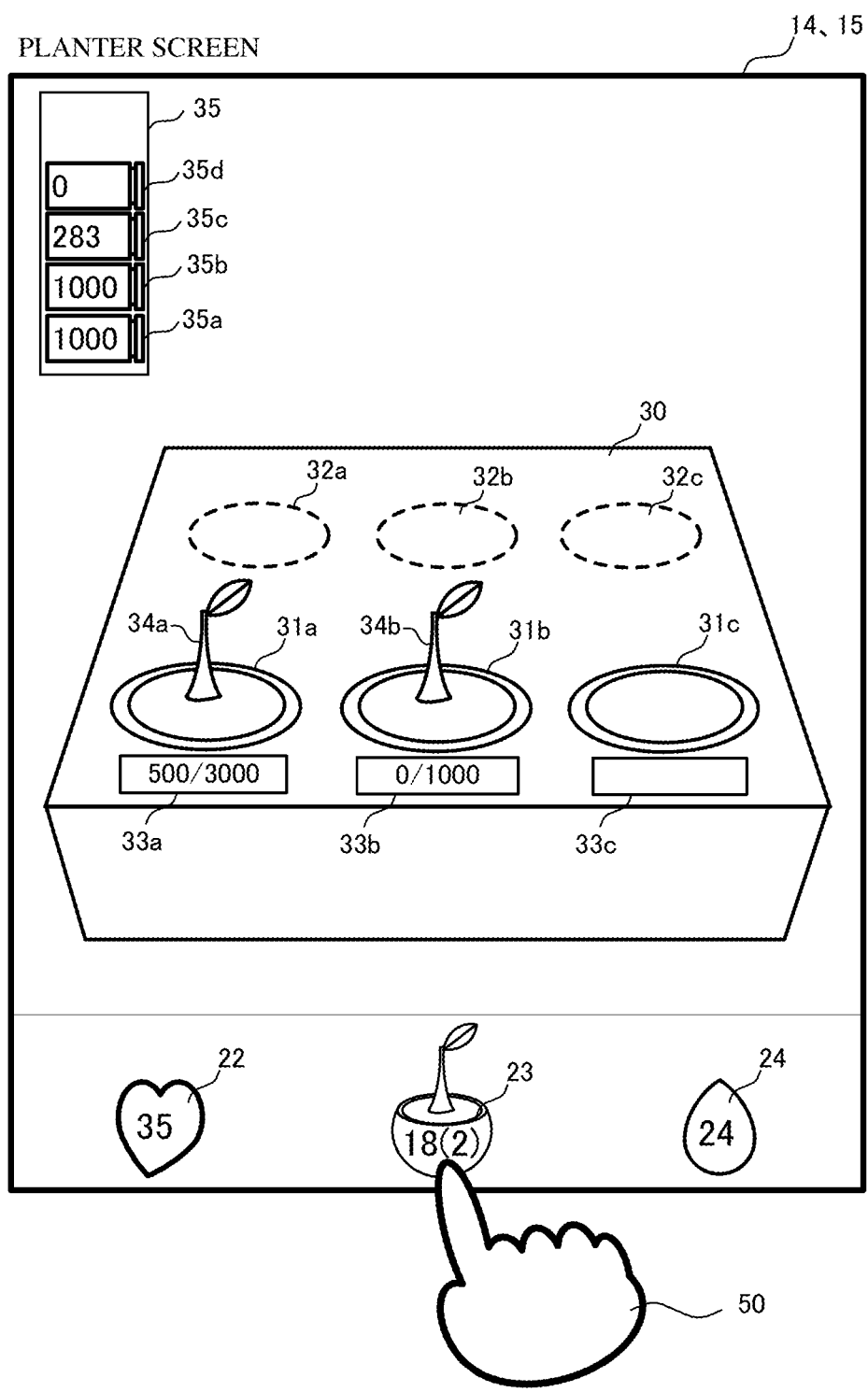
FIG. 4 shows a non-limiting example of a game screen.

FIG. 4 shows an example of the planter screen. When the menu screen has shifted to the planter screen in accordance with a user's operation, as shown in FIG. 4, the planter screen is displayed. On the planter screen, a planter image 30 (which may be simply referred to as "planter") for growing seedlings, and a step tank image 35 (which may be simply referred to as "step tank") in which steps the user has walked with the information processing apparatus 10 carried are accumulated, are displayed. As shown in FIG. 4, in the planter image 30, there are three seedling plantable parts (31a, 31b, 31c) which have been present originally (initially) and where seedlings can be planted, and three extensible parts (32a, 32b, 32c) which can be added as parts where seedlings can be planted. The user can increase the number of seedling plantable parts to six at maximum by performing an operation (which may be referred to as "planter extending operation") of using in-game coins (in-game currency, which may be simply referred to as "coins"; not shown). The user can acquire coins in accordance with the elapsed period since this game was initially started, payment, or the like. In addition, as in the menu screen described in FIG. 2, at the lower part of the planter screen, the petal count image 22, the seedling count image 23, and the nectar count image 24 are displayed.

The user can plant a possessed seedling in the planter image 30. As shown in FIG. 4, when the user taps the seedling count image 23, in accordance with the number of times of the tap operation, seedlings are planted in the seedling plantable parts 31 of the planter image 30, and the number of the planted seedlings are indicated in parentheses in the seedling count image 23. In the example shown in FIG. 4, in a state in which the seedling image 34a has been already planted in the seedling plantable part 31a of the planter image 30, the user performs operation (which may be referred to as "seedling planting operation") of tapping the seedling count image 23 once, whereby the seedling image 34b (which may be simply referred to as "seedling") is planted in the seedling plantable part 31b and the number in the parentheses in the seedling count image 23 is incremented from 1 to 2. In FIG. 4, the number of seedling plantable parts is three, and it is impossible to plant more than three seedlings.

As shown in FIG. 4, at each seedling plantable part (31a, 31b, 31c), a seedling accumulated step count image (33a, 33b, 33c) is displayed. The seedling accumulated step count image (33a, 33b, 33c) indicates the number of steps having been accumulated for the corresponding seedling (the number of steps the user has walked with the information processing apparatus 10 carried) since the time when the seedling was planted, and the number of steps needed until the seedling grows to be a character. Thus, the seedling accumulated step count image 33 can also be said to be an image indicating the growth degree of the seedling. In the example shown in FIG. 4, in the seedling accumulated step count image 33a, 500 is indicated as the number of steps having been accumulated for the seedling since the time when the seedling was planted, and 3000 is indicated as the number of steps needed until the seedling grows to be a character. In addition, in the seedling accumulated step count image 33b, 0 is indicated as the number of steps having been accumulated for the seedling since the time when the seedling was planted, and 1000 is indicated as the number of steps needed until the seedling grows to be a character. Thus, the number of steps needed until the seedling grows to be a character may differ depending on the seedling. In the seedling plantable part 31c, no seedling is planted and therefore such numbers are not indicated in the seedling accumulated step count image 33c.

As shown in FIG. 4, the step tank image 35 is displayed in which steps the user has walked with the information processing apparatus 10 carried are accumulated. The step tank image 35 is composed of up to five unit step tank images (35a, etc., which may be simply referred to as "unit step tank"). In the unit step tank image, steps taken by the user can be accumulated by up to 1000. In addition, the user can perform operation (which may be referred to as "step tank increasing operation") of increasing the number of unit step tank images to five at maximum by using coins. In the example shown in FIG. 4, the step tank image 35 is composed of four unit step tank images (35a, 35b, 35c, 35d). A number 1000 which indicates that 1000 steps are accumulated is indicated in the unit step tank images 35a and 35b, a number 283 which indicates that 283 steps are accumulated is indicated in the unit step tank image 35c, and a number 0 which indicates that no steps are accumulated is indicated in the unit step tank image 35d. Thus, it is indicated that 2283 steps are accumulated in total.

Figure 5:
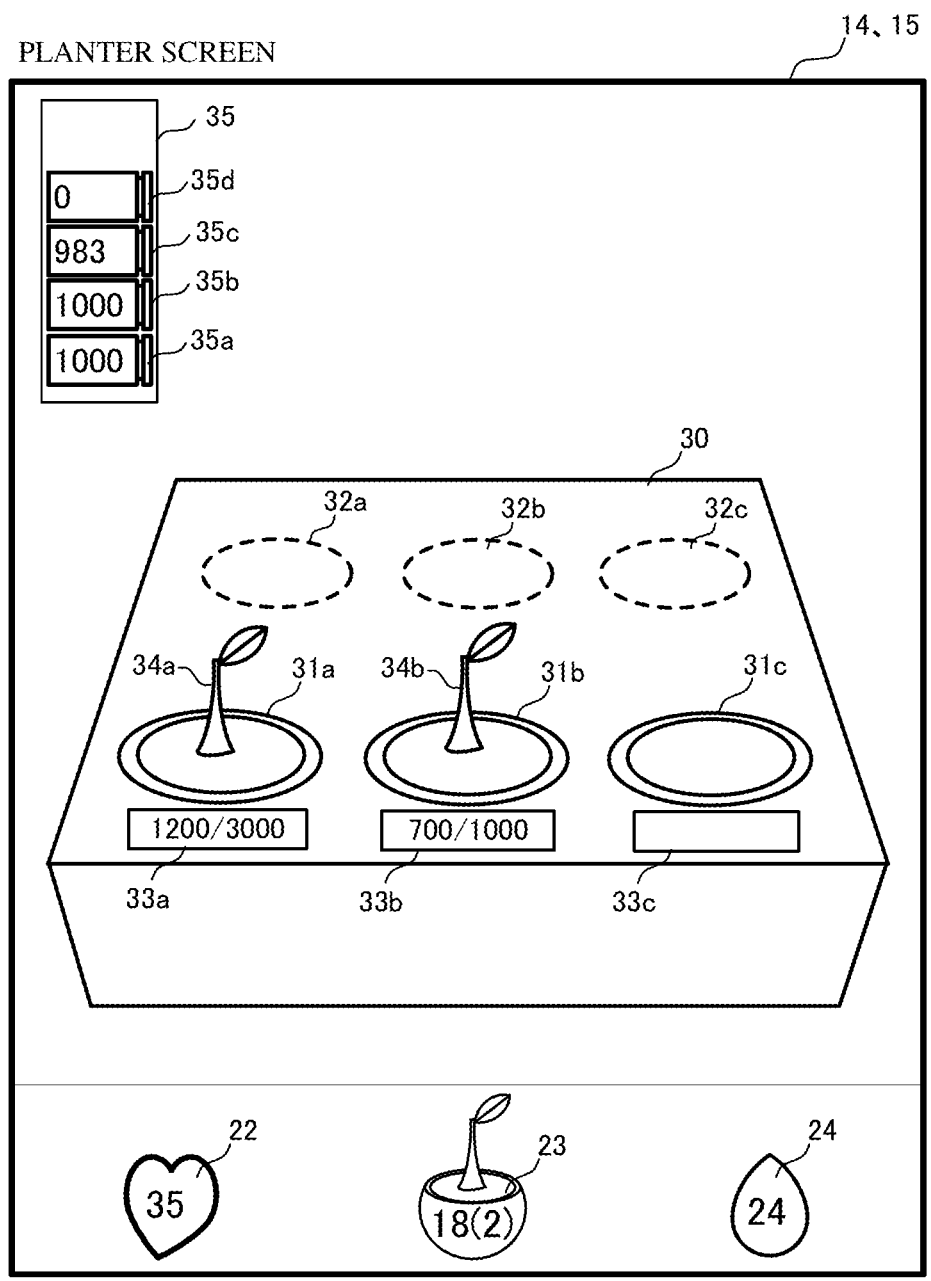
FIG. 5 shows a non-limiting example of a game screen.

FIG. 5 shows an example of the planter screen. Hereinafter, with reference to FIG. 5, a case where the user walks with the information processing apparatus 10 carried and steps are accumulated in the seedling accumulated step count images 33 and the step tank image 35 will be described. When the user walks with the information processing apparatus 10 carried, steps are accumulated in each seedling accumulated step count image 33 and the step tank image 35 simultaneously. In the example shown in FIG. 5, the user has walked 700 steps with the information processing apparatus 10 carried from the state in FIG. 4, so that 700 steps are accumulated in each of the seedling accumulated step count image 33a, the seedling accumulated step count image 33b, and the step tank image 35. That is, in accordance with the number of steps the user has walked, each seedling grows and steps are accumulated in the step tank. In each seedling accumulated step count image 33, steps exceeding the number of steps (e.g., 1000 in the seedling accumulated step count image 33b) needed until the seedling grows to be a character, are not accumulated.

Figure 6:
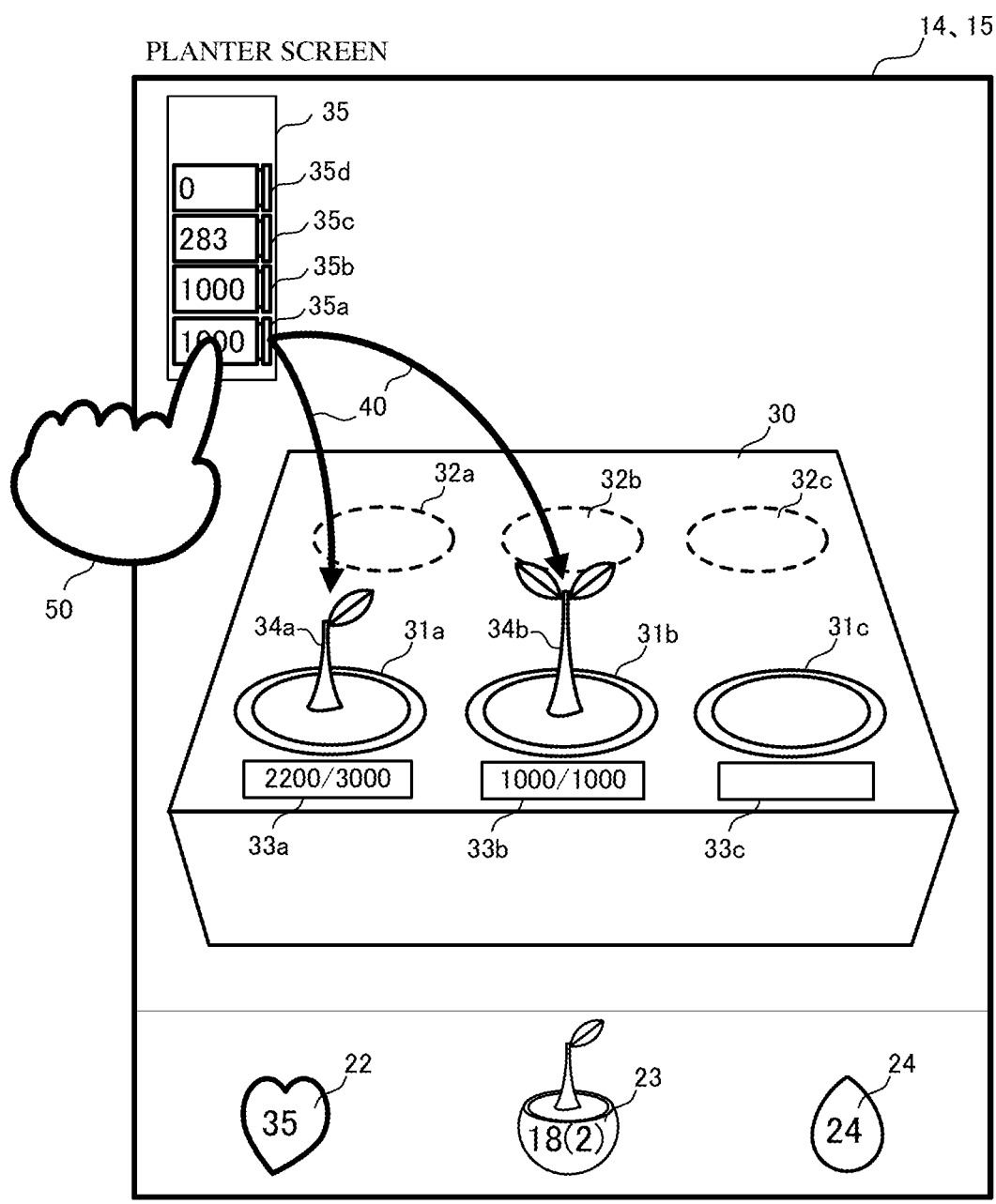
FIG. 6 shows a non-limiting example of a game screen.

FIG. 6 shows an example of the planter screen. Hereinafter, with reference to FIG. 6, a case where steps accumulated in the step tank image 35 are given to the seedling image 34 to grow the seedling, will be described. As shown in FIG. 6, the user performs tap operation (which may be referred to as "step tank use operation") on the unit step tank image (35a, etc.) in which 1000 steps are accumulated, in the step tank image 35, whereby images 40 for giving the steps accumulated in the unit step tank image to the respective seedling images 34 are displayed and this unit step tank image is deleted, so that 1000 steps are accumulated in the respective seedling accumulated step count images 33 corresponding to the seedling images 34. Here, an upper limit accumulated step count for each unit step tank image is 1000, and only the unit step tank image that has reached the upper limit accumulated step count 1000 can be used to give steps to the seedling images 34 in accordance with tap operation, only on a 1000-step basis. In the example shown in FIG. 6, by the user performing tap operation on the unit step tank image 35a that has reached the upper limit accumulated step count 1000, the unit step tank image 35a is deleted (consumed), and as a result, 1000 steps are accumulated in the seedling accumulated step count image 33a of the seedling image 34a so that the number of the accumulated steps has increased from 1200 steps (see FIG. 5) to 2200 steps, and 1000 steps are accumulated in the seedling accumulated step count image 33b of the seedling image 34b so that the number of the accumulated steps has increased from 700 steps (see FIG. 5) to 1000 steps. Here, as previously described, in each seedling accumulated step count image 33, steps exceeding the number of steps (upper limit step count) needed until the seedling grows to be a character are not accumulated. Therefore, in the seedling accumulated step count image 33b, steps are accumulated to 1000 steps corresponding to the upper limit. In addition, as shown in FIG. 6, the seedling image 34b corresponding to the seedling accumulated step count image 33b in which 1000 steps corresponding to the upper limit are accumulated is changed into a double-leaf state showing that the seedling has fully grown (growth of the seedling is finished).

Figure 7:
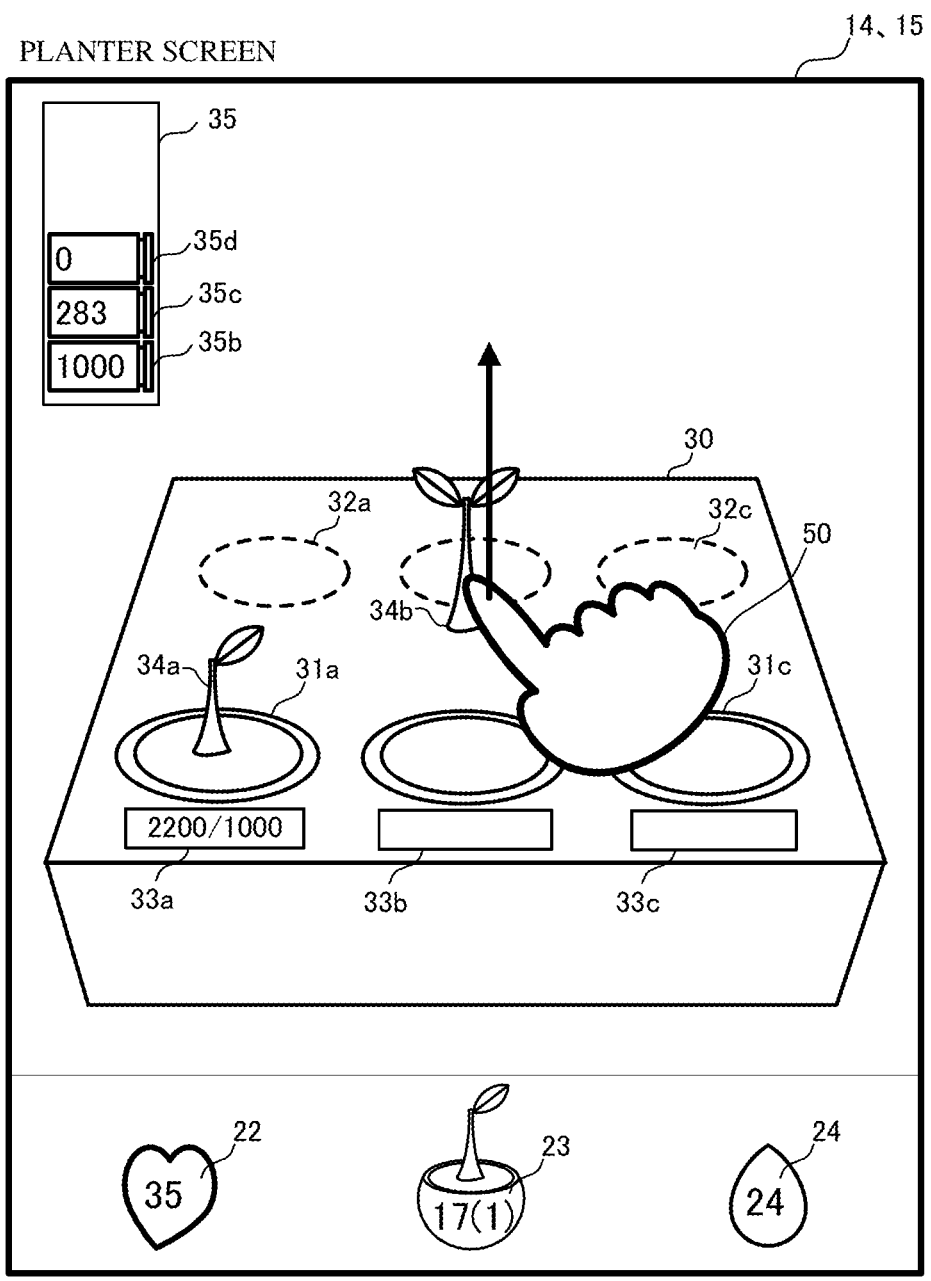
FIG. 7 shows a non-limiting example of a game screen.

FIG. 7 shows an example of the planter screen. Hereinafter, with reference to FIG. 7, a case where the seedling image 34 the growth of which is finished is plucked to be a character image will be described. As shown in FIG. 7, the user performs swipe operation (operation of touching and sliding, which may be referred to as "plucking operation") upward on the seedling image 34 the growth of which is finished, and accordingly, a scene in which the seedling image 34 is plucked is displayed, and the number of possessed seedlings indicated on the seedling count image 23 and the number written in parentheses and indicating the number of seedlings planted in the planter 30, are decremented by 1. In addition, the numbers on the seedling accumulated step count image 33 corresponding to the plucked seedling image 34 are deleted. In the example shown in FIG. 7, in accordance with the user's swipe operation, the seedling image 34b the growth of which is finished is plucked, the numbers indicated on the seedling count image 23 are decremented from 18(2) to 17(1), and the numbers on the seedling accumulated step count image 33b are deleted. The plucked seedling image 34 is changed to a character image 40a described later. In addition, in FIG. 7, since the unit step tank image 35a is used in FIG. 6, the unit step tank image 35a is deleted and the other unit step tanks are shifted downward. The seedling image 34 the growth of which has not been finished cannot be plucked (prohibited from being plucked).

Figure 8:
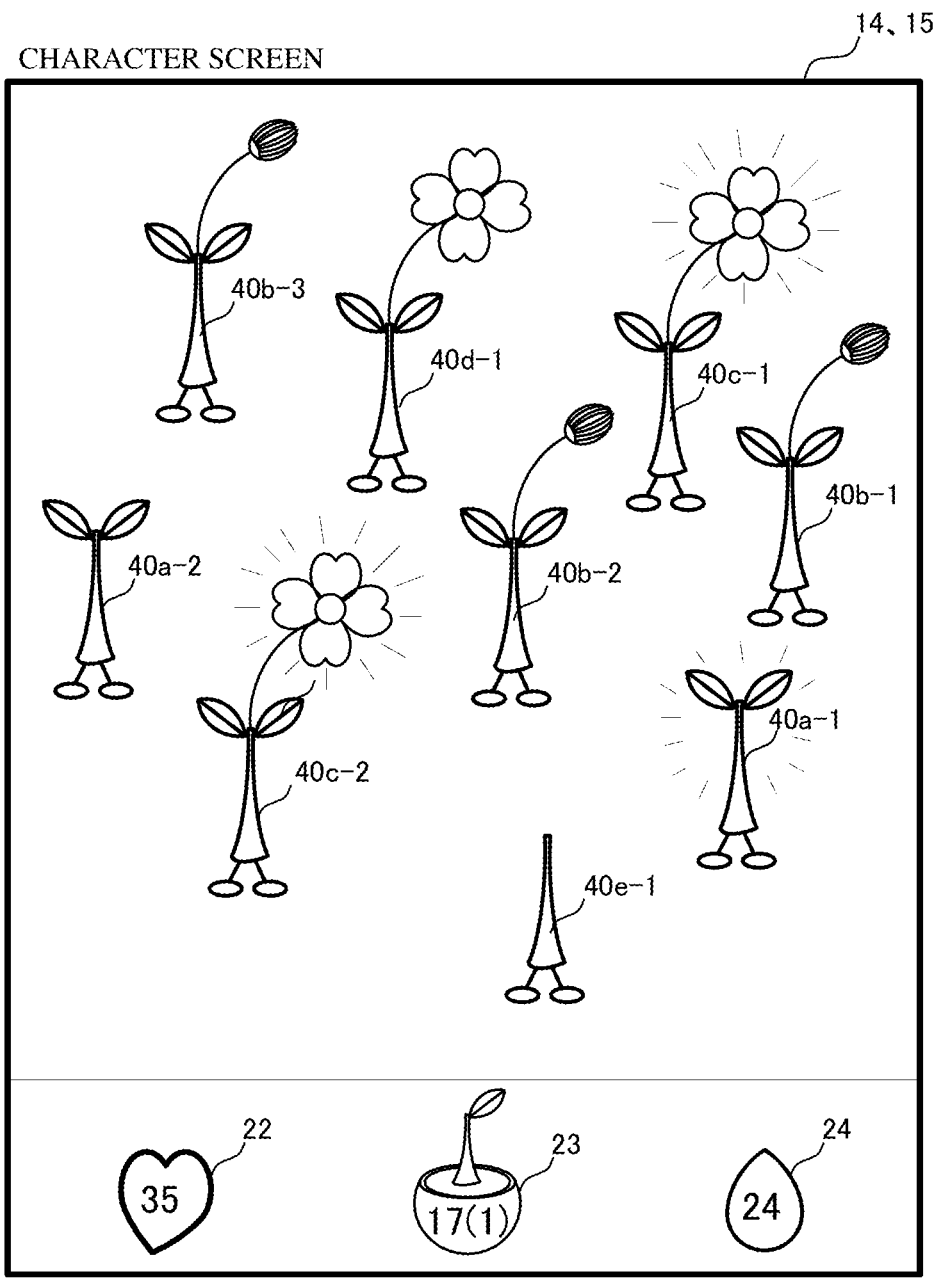
FIG. 8 shows a non-limiting example of a game screen.

FIG. 8 shows an example of the character screen. Hereinafter, with reference to FIG. 8, the details of the character screen will be described. On the character screen, character images 40 (which may be simply referred to as "character" or "char") acquired by plucking the seedling image 34 the growth of which is finished (see FIG. 7), are displayed. As shown in FIG. 8, the character images 40 include a character image 40a in a double-leaf state, a character image 40b in a bud state, a character image 40c in a glowing flower state in which a glowing flower is bloomed, a character image 40d in a flower state in which a flower not glowing is bloomed, and a character image 40e in a leafless state of having no leaves. In the example shown in FIG. 8, character images (40a-1, 40a-2) in a double-leaf state, character images (40b-1, 40b-2, 40b-3) in a bud state, character images (40c-1, 40c-2) in a glowing flower state, a character image (40d-1) in a flower state, and a character image (40e-1) in a leafless state, are displayed. As shown in FIG. 8, the character image (40a-1) in a double-leaf state, which is newly displayed by plucking the seedling image 34 the growth of which is finished, is displayed in a glowing manner so that this fact is understandable. In addition, as in the menu screen described in FIG. 2, at the lower part of the character screen, the petal count image 22, the seedling count image 23, and the nectar count image 24 are displayed.

Figure 9:
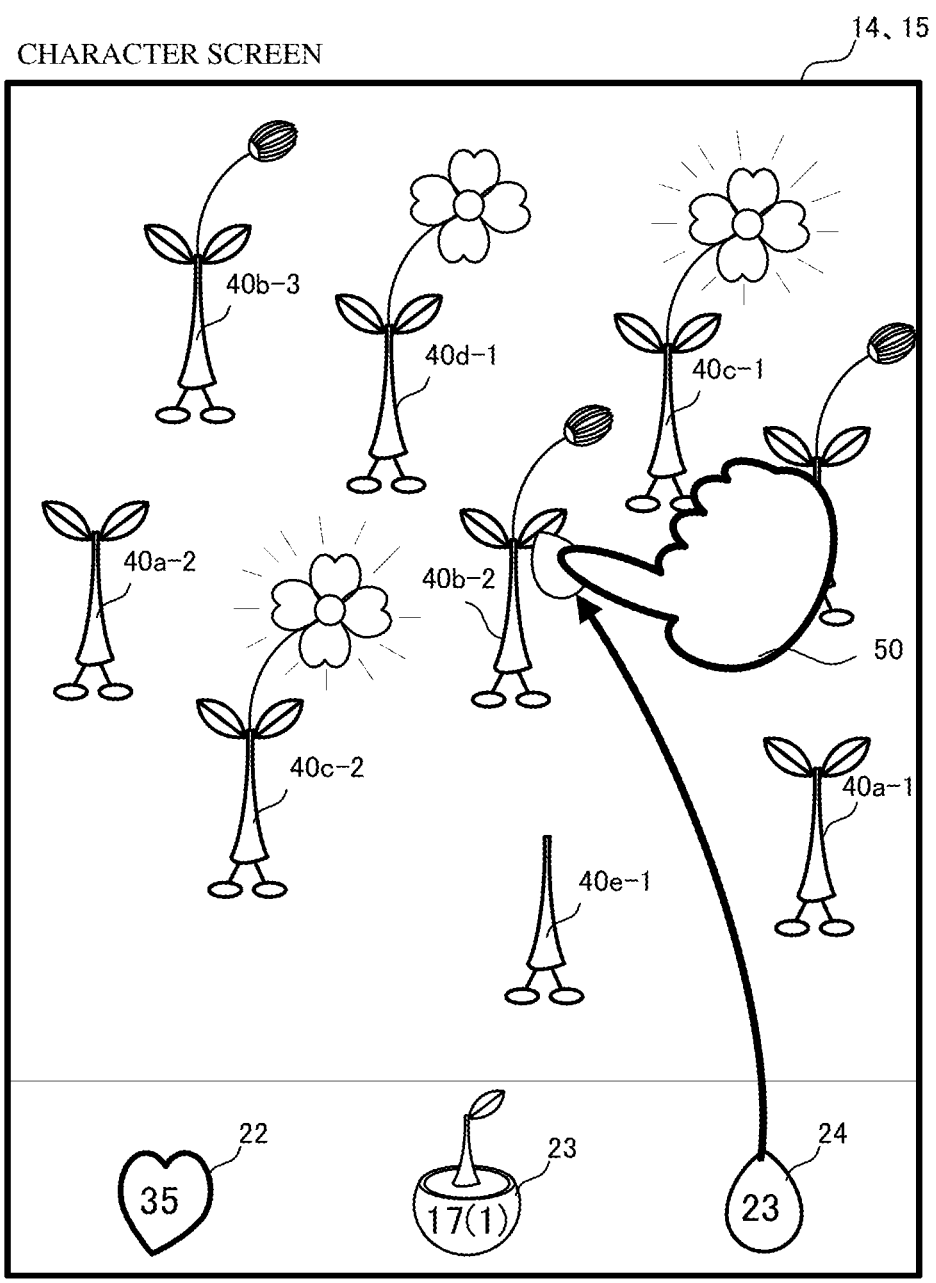
FIG. 9 shows a non-limiting example of a game screen.

FIG. 9 shows an example of the character screen. Hereinafter, with reference to FIG. 9, a case where possessed nectar is fed to a character displayed on the character screen will be described. Here, nectar can be fed to the character image 40a in a double-leaf state, the character image 40b in a bud state, and the character image 40d in a flower state, whereas nectar cannot be fed to the character image 40c in a glowing flower state and the character image 40e in a leafless state. In addition, as described later, when nectar is fed, the character image 40a in a double-leaf state is immediately changed to the character image 40b in a bud state, the character image 40b in a bud state is immediately changed to the character image 40c in a glowing flower state, and the character image 40d in a flower state is immediately changed to the character image 40c in a glowing flower state.

As shown in FIG. 9, when swipe operation (which may be referred to as "nectar feeding operation") is performed from the nectar count image 24 toward the character image 40 that can be changed (a character that can be fed with nectar), an image of nectar moves toward the character image 40, the number of possessed nectars on the nectar count image 24 is decremented, and the state of this character image 40 is changed. In the example shown in FIG. 9, nectar feeding operation is performed to feed nectar to the character image 40b-2 in a bud state, so that the number of possessed nectars on the nectar count image 24 is decremented from 24 to 23, and the character image 40b-2 in a bud state is changed to a glowing flower state (not shown).

Figure 10:
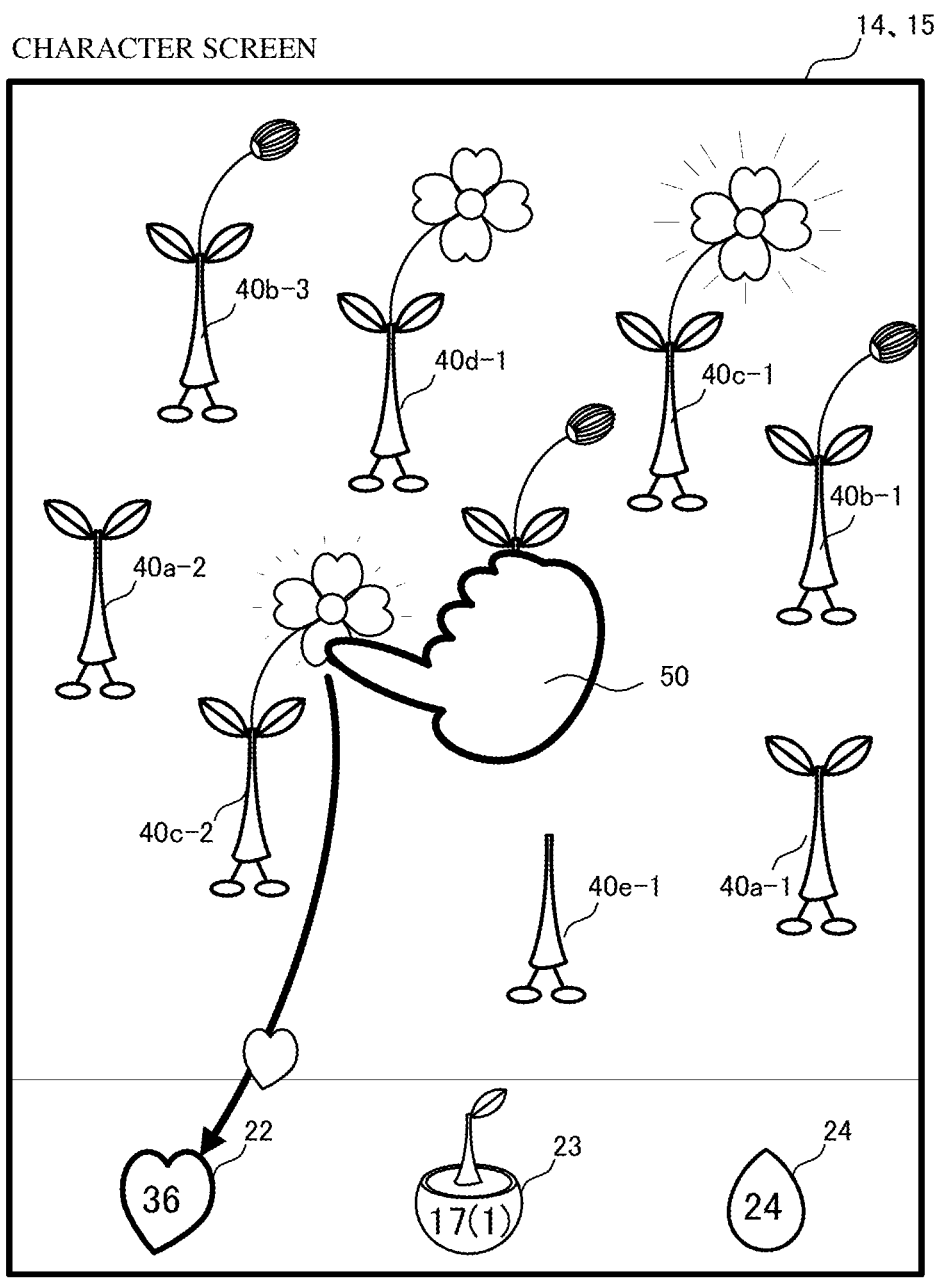
FIG. 10 shows a non-limiting example of a game screen.

FIG. 10 shows an example of the character screen. Hereinafter, with reference to FIG. 10, a case where a petal is obtained (picked) from the character image 40c in a glowing flower state will be described. Here, a petal can be picked from the character image 40c in a glowing flower state, but cannot be picked from the character image 40d in a flower state (and the character images in the other states).

As shown in FIG. 10, when the user performs tap operation (which may be referred to as "petal obtaining operation") on the character image 40c in a glowing flower state, an image of a petal moves toward the petal count image 22, the number of possessed petals on the petal count image 22 is incremented, and the character image 40c in the glowing flower state changes to a flower state (40d) or a leafless state (40e). In the example shown in FIG. 10, petal obtaining operation is performed on the character image 40c-2 in a glowing flower state, so that the number of possessed petals on the petal count image 22 is incremented from 35 to 36, and the character image 40c-2 in a glowing flower state is changed to a flower state (not shown).

Figure 11:
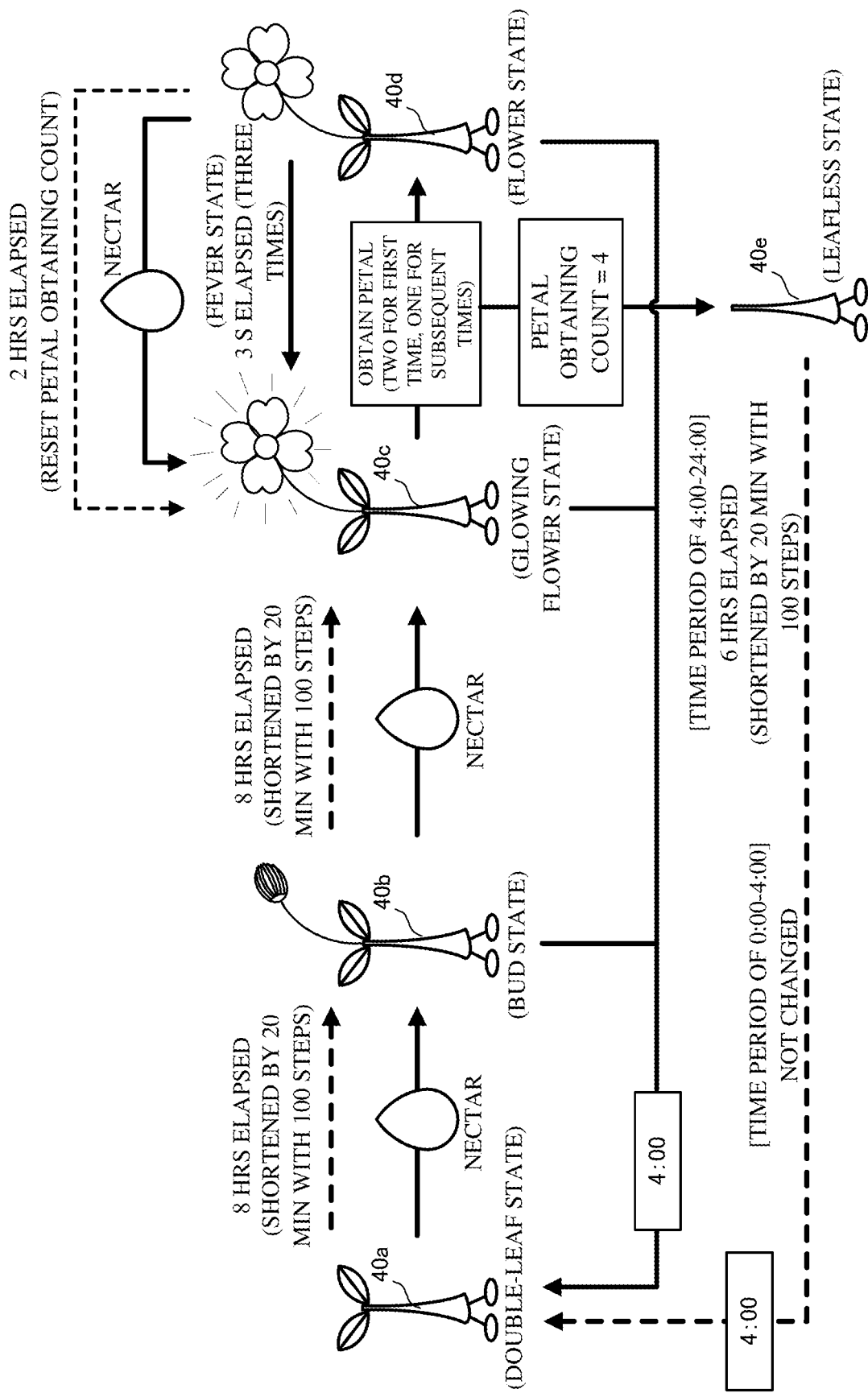
FIG. 11 illustrates state change of a game character.

FIG. 11 schematically illustrates state change of the character 40 displayed on the character screen described in FIG. 8, etc. Hereinafter, with reference to FIG. 11, state change of the character 40 will be described.

When nectar is fed to the character image 40a in a double-leaf state (see FIG. 9), the character image 40a immediately changes (grows) to the character image 40b in a bud state. Besides, when eight hours have elapsed since the time when the character state came into a double-leaf state, the character image 40a in a double-leaf state changes to the character image 40b in a bud state. Here, the period (eight hours) needed for this change is shortened by 20 minutes per 100-count increase in the number of steps taken from the time when the character state came into a double-leaf state (the number of steps the user has walked with the information processing apparatus 10 carried). For example, in a case where the number of steps taken from the time when the character state came into a double-leaf state is 633, the period (eight hours) required for the above change is shortened by two hours, to be six hours.

When nectar is fed to the character image 40b in a bud state (see FIG. 9), the character image 40b immediately changes (grows) to the character image 40c in a glowing flower state. Besides, when eight hours have elapsed since the character state came into a bud state, the character image 40b in a bud state changes to the character image 40c in a glowing flower state. Here, the period (eight hours) needed for this change is shortened by 20 minutes per 100-count increase in the number of steps taken from the time when the character state came into a bud state (the number of steps the user has walked with the information processing apparatus 10 carried). For example, in a case where the number of steps taken from when the character state came into a bud state is 685, the period (eight hours) needed for the above change is shortened by two hours, to be six hours.

From the character image 40c in a glowing flower state, the user can obtain (pick) a petal by petal obtaining operation (see FIG. 10). The character image 40c in a glowing flower state after the user has obtained the petal changes to the character image 40d in a flower state in which the user cannot obtain a petal. If nectar feeding operation is performed on the character image 40d in a flower state (see FIG. 9), the character image 40d returns to the character image 40c in a glowing flower state so that the user can obtain a petal. Besides, when two hours have elapsed since the time when the character image changed to the character image 40d in a flower state, the character image 40d returns to the character image 40c in a glowing flower state so that the user can obtain a petal. After the bud state has changed to the glowing flower state, the user is allowed to perform petal obtaining operation four times. However, in a case where two hours have elapsed since the time when the character image changed to the character image 40d in a flower state and thus the character image 40d returns to the character image 40c in a glowing flower state as described above, the number of times the petal obtaining operation has been performed is reset so that the user can perform petal obtaining operation four times again. In addition, in a case where the user performs petal obtaining operation for the first time since the bud state changed to the glowing flower state, the user obtains two petals, and after that, when the user performs petal obtaining operation three times (or four times if the number of times for petal obtaining operation is reset with elapse of two hours), the user obtains one petal for each time. Then, after petal obtaining operation has been performed four times, the character image 40c in a glowing flower state changes to the character image 40e in a leafless state.

Meanwhile, the character image 40c that has changed to a glowing flower state from a double-leaf state without being fed with nectar comes into a fever state with a predetermined probability (e.g., 10%). For the character image 40c in a glowing flower state that has come into a fever state, the fever state is canceled after such a loop that the character state changes to a flower state by the user obtaining petals and then returns to a glowing flower state in three seconds is repeated three times.

In a time period from 4:00 to 24:00, when six hours have elapsed since the time when the character state came into a leafless state, the character image 40e in a leafless state returns to the character image 40a in a double-leaf state. On the other hand, in a time period from 0:00 (24:00) to 4:00, even if six hours have elapsed since the time when the character state came into a leafless state, the character image 40e in a leafless state does not return to the character image 40a in a double-leaf state. Here, the above period (six hours) to elapse is shortened by 20 minutes per 100-count increase in the number of steps that have been taken in the time period from 4:00 to 24:00 and that have been taken since the time when the character state came into a leafless state (the number of steps the user has walked with the information processing apparatus 10 carried). For example, in a case where the character state has come into a leafless state at 19:00 and then the user has walked 600 steps during a time period from 21:00 to 22:00, the period to elapse is shortened by two hours and thus the character state returns to the character image 40a in a double-leaf state at 23:00. In addition, the character image 40b in a bud state, the character image 40c in a glowing flower state, the character image 40d in a flower state, and the character image 40e in a leafless state return to the character image 40a in a double-leaf state at 4:00. In addition, for the character image 40a in a double-leaf state, the elapsed period since the character state came into a double-leaf state is reset at 4:00.

[Details of Information Processing in Exemplary Embodiment]

Next, with reference to FIG. 12 to FIG. 16, the information processing in the exemplary embodiment will be described in detail.

[Used Data]

Figure 12:
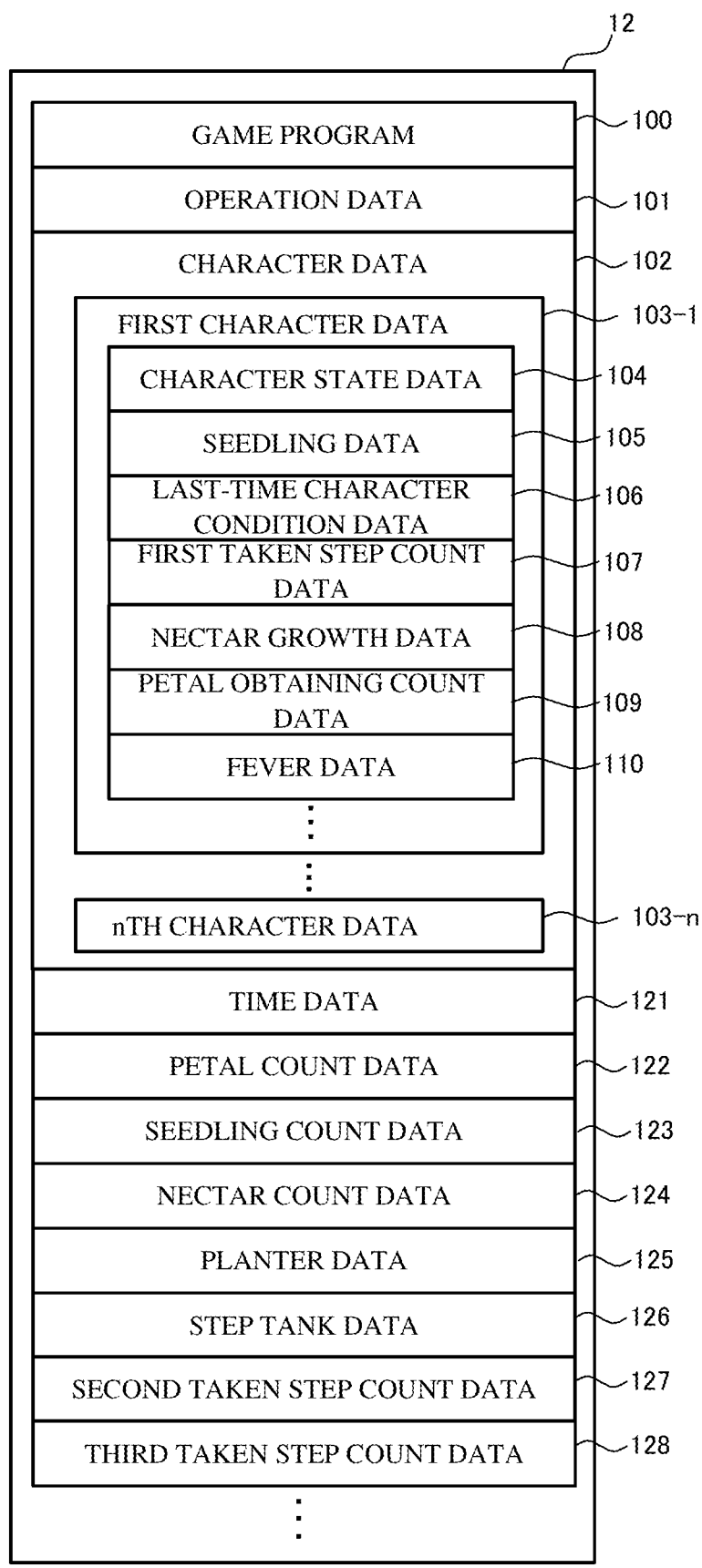
FIG. 12 shows a non-limiting example of a program and data stored in a memory 12 of the information processing apparatus 10.

Various data used in this game process will be described. FIG. 12 shows an example of a program and data stored in the memory 12 of the information processing apparatus 10. The memory 12 stores a game program 100, operation data 101, character data 102, time data 121, petal count data 122, seedling count data 123, nectar count data 124, planter data 125, step tank data 126, second taken step count data 127, third taken step count data 128, and the like.

The game program 100 is a game program for executing the game process according to the exemplary embodiment.

The operation data 101 is data indicating operation performed on the information processing apparatus 10, which is input operation to a touch panel, for example.

The character data 102 is data regarding characters 40 and seedlings which will become characters 40, as described with reference to FIG. 3 to FIG. 11. The character data 102 includes first to nth (n is a natural number) character data (103-1 to 103-n). That is, the character data 103 is generated for each character 40 (or each seedling that will become the character 40) in this game. Hereinafter, the first character data 103-1 will be described. For the second to nth character data 103-2 to 103-n, the same kinds of data as the first character data 103-1 are stored.

The first character data 103-1 includes character state data 104, seedling data 105, last-time character condition data 106, first taken step count data 107, nectar growth data 108, petal obtaining count data 109, and fever data 110.

The character state data 104 is data indicating the state of the character. Specifically, the character state data 104 is data indicating the state of the character 40 (double-leaf state, bud state, glowing flower state, flower state, or leafless state; see FIG. 11), and indicating the state of a seedling that will become the character 40 (including information about whether or not the seedling is planted in the planter 30; see FIG. 4). In the exemplary embodiment, also a character in a seedling state may be referred to as "character".

The seedling data 105 is data indicating the upper limit number of steps (number of steps with which growth of the seedling is finished) that can be accumulated for the seedling (character in a seedling state), and indicating the number of steps accumulated for the seedling. The upper limit number of steps that can be accumulated may differ among seedlings, and for example, fixed numbers of steps such as 1000 and 3000 are set (see FIG. 4).

The last-time character condition data 106 is data indicating the state of the character at the time when the character screen was displayed last time (i.e., the time at which the state of the character was determined when the character screen was displayed last time) (this state may be referred to as "character state at last-time display"), and if this state can change to the next state with elapse of a period, indicating a scheduled remaining period until change to the next state (which may be referred to as "next-change scheduled remaining period"). That is, the last-time character condition data 106 indicates the condition of the character at the time when the character screen was displayed last time (which may be referred to as "character condition at last-time display").

The first taken step count data 107 is data indicating the number of steps the user has walked (or run) with the information processing apparatus 10 carried. Specifically, the first taken step count data 107 is data indicating the number of steps (number of steps calculated on the basis of a detection result from the detection section 16) taken from the time when the character screen was displayed last time (i.e., the time at which the state of the character was determined when the character screen was displayed last time), and the number of steps taken as described above (which may be referred to as "number of taken steps") is accompanied with information about time (period) when the steps are taken. That is, the first taken step count data 107 indicates a time history of the number of taken steps. For example, in a case where 150 steps are taken during one minute (unit period) from 13:00 to 13:01 on Jan. 1, 2021, the number of taken steps, i.e., 150 steps, is associated with the period when the steps are taken (from 13:00 to 13:01 on Jan. 1, 2021). In the exemplary embodiment, the period when the steps are taken is described using one minute as a unit period, but in another exemplary embodiment, the unit period may be one second, for example.

The nectar growth data 108 is information indicating whether or not the character 40 has ever changed by being fed with nectar in a process of changing from a double-leaf state to a glowing flower state (see FIG. 11).

The petal obtaining count data 109 is information indicating the number of times a petal has been obtained from the character 40c in a glowing flower state (this can be also said to be the number of times of petal obtaining operation, and may be referred to as "petal obtaining count") (see FIG. 11).

The fever data 110 is data regarding the fever state described with reference to FIG. 11. Specifically, the fever data 110 includes data (e.g., flag data) indicating whether or not the character 40 is in a fever state, data indicating how many times the character 40 has returned to a glowing flower state (in three seconds) after coming into a fever state, and data indicating the upper limit number of times, i.e., three times, for returning to a glowing flower state (in three seconds) in a fever state.

Thus, description of the character data 102 has been finished.

The time data 121 is information indicating the present time (present date and time).

The petal count data 122 is data indicating the number of possessed petals. On the basis of the petal count data 122, the number of possessed petals is displayed on the petal count image 22 (see FIG. 3, etc.).

The seedling count data 123 is data indicating the number of possessed seedlings. On the basis of the seedling count data 123, the number of possessed seedlings is displayed on the seedling count image 23 (see FIG. 3, etc.).

The nectar count data 124 is data indicating the number of possessed nectars. On the basis of the nectar count data 124, the number of possessed nectars is displayed on the nectar count image 24 (see FIG. 3, etc.).

The planter data 125 is data regarding a planter described in FIG. 4, etc. Specifically, the planter data 125 includes data indicating the number (initially, three) of seedling plantable parts where seedlings can be planted in the planter 30, data indicating the number (three at maximum) of extensible parts that can be added as parts where seedlings can be planted, and data indicating the number of seedlings planted in the seedling plantable parts.

The step tank data 126 is data regarding a step tank (step tank image 35) described in FIG. 5, FIG. 6, etc. Specifically, the step tank data 126 includes data indicating the number (five at maximum) of unit step tanks (unit step tank image 35a, etc.) composing the step tank, and data indicating the number of steps accumulated in each unit step tank (which may be referred to as "number of accumulated steps"; the upper limit number thereof is 1000).

The second taken step count data 127 is data indicating the number of steps the user has walked (or run) with the information processing apparatus 10 carried. Specifically, the second taken step count data 127 is data indicating the number of steps (number of steps calculated on the basis of a detection result from the detection section 16) taken from the time when the acquisition notice screen shown in FIG. 3(2) was displayed last time.

The third taken step count data 128 is data indicating the number of steps the user has walked (or run) with the information processing apparatus 10 carried. Specifically, the third taken step count data 123 is data indicating the number of steps (number of steps calculated on the basis of a detection result from the detection section 16) taken from the time when the planter screen shown in FIG. 4, etc. was displayed last time.

Here, in the information processing apparatus 10, a step counting application is installed, besides the application of this game. During a period in which the information processing apparatus 10 is operating, the step counting application works to always count the number of steps taken by the user walking (or running) on the basis of information from the detection section 16, and store the number of steps in the memory in association with the time period in which the counted steps have been taken. That is, the step counting application is generating time history data (not shown) of the number of taken steps during the operating period of the information processing apparatus 10. Then, in this game process, using the time history data of the number of taken steps as appropriate, the first taken step count data 107, the second taken step count data 127, and the third taken step count data 128 are generated (updated).

[Details of Game Process]

Next, with reference to flowcharts, the details of the game process according to the exemplary embodiment will be described. FIG. 13 to FIG. 16 are examples of flowcharts showing the details of the game process according to the exemplary embodiment.

[Process for Menu Screen]

Figure 13:
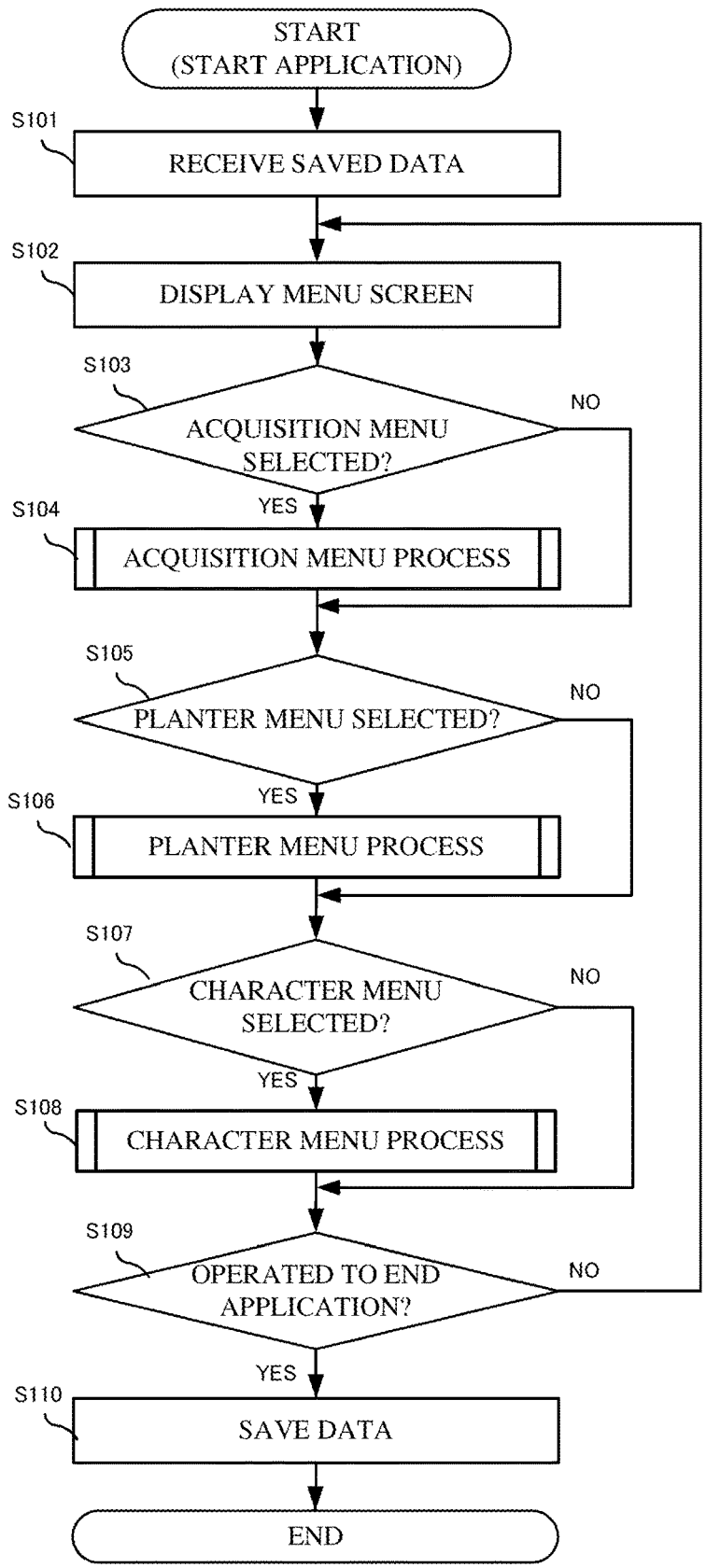
FIG. 13 is a non-limiting example of a flowchart showing the details of a game process.

First, when operation of starting the application of this game is performed, a process shown in FIG. 13 is started.

In step S101 in FIG. 13, the processor 11 receives saved data from a game server (not shown) by, for example, wireless communication via the Internet, and loads the saved data to the respective data stored in the memory 12. Then, the process proceeds to step S102.

In step S102, the processor 11 displays the menu screen on the display section 15 (see FIG. 2). Then, the process proceeds to step S103.

In step S103, the processor 11 determines whether or not operation of selecting the acquisition menu has been performed. Specifically, the processor 11 determines whether or not the acquisition menu image 17*a* is touched on the menu screen, on the basis of the operation data (see FIG. 12). In the case of YES in this determination, the process proceeds to step S104, and in the case of NO in this determination, the process proceeds to step S105.

In step S104, the processor 11 performs an acquisition menu process for acquiring a seedling or nectar described in FIG. 3. The acquisition menu process will be described later with reference to FIG. 14. Then, the process proceeds to step S105.

In step S105, the processor 11 determines whether or not operation of selecting the planter menu has been performed. Specifically, the processor 11 determines whether or not the planter menu image 17*b* is touched on the menu screen, on the basis of the operation data. In the case of YES in this determination, the process proceeds to step S106, and in the case of NO in this determination, the process proceeds to step S107.

In step S106, the processor 11 performs a planter menu process for growing a seedling in the planter 30 described in FIG. 4 to FIG. 7. The planter menu process will be described later with reference to FIG. 15. Then, the process proceeds to step S107.

In step S107, the processor 11 determines whether or not operation of selecting the character menu has been performed. Specifically, the processor 11 determines whether or not the character menu image 17*c* is touched on the menu screen, on the basis of the operation data. In the case of YES in this determination, the process proceeds to step S108, and in the case of NO in this determination, the process proceeds to step S109.

In step S108, the processor 11 performs a character menu process for growing the character 40 and obtaining a petal as described in FIG. 8 to FIG. 11. The character menu process will be described later with reference to FIG. 16. Then, the process proceeds to step S109.

In step S109, the processor 11 determines whether or not predetermined application ending operation has been performed. Specifically, the processor 11 determines whether or not the application ending operation has been performed on the basis of the operation data. In the case of YES in this determination, the process proceeds to step S110, and in the case of NO in this determination, the process returns to step S102 to continue to display the menu screen.

In step S110, the processor 11 saves data regarding this game, and then ends the game process. Specifically, the processor 11 saves data stored in the memory 12, into the game server, by, for example, wireless communication via the Internet, and then ends the application of this game.

[Acquisition Menu Process]

Figure 14:
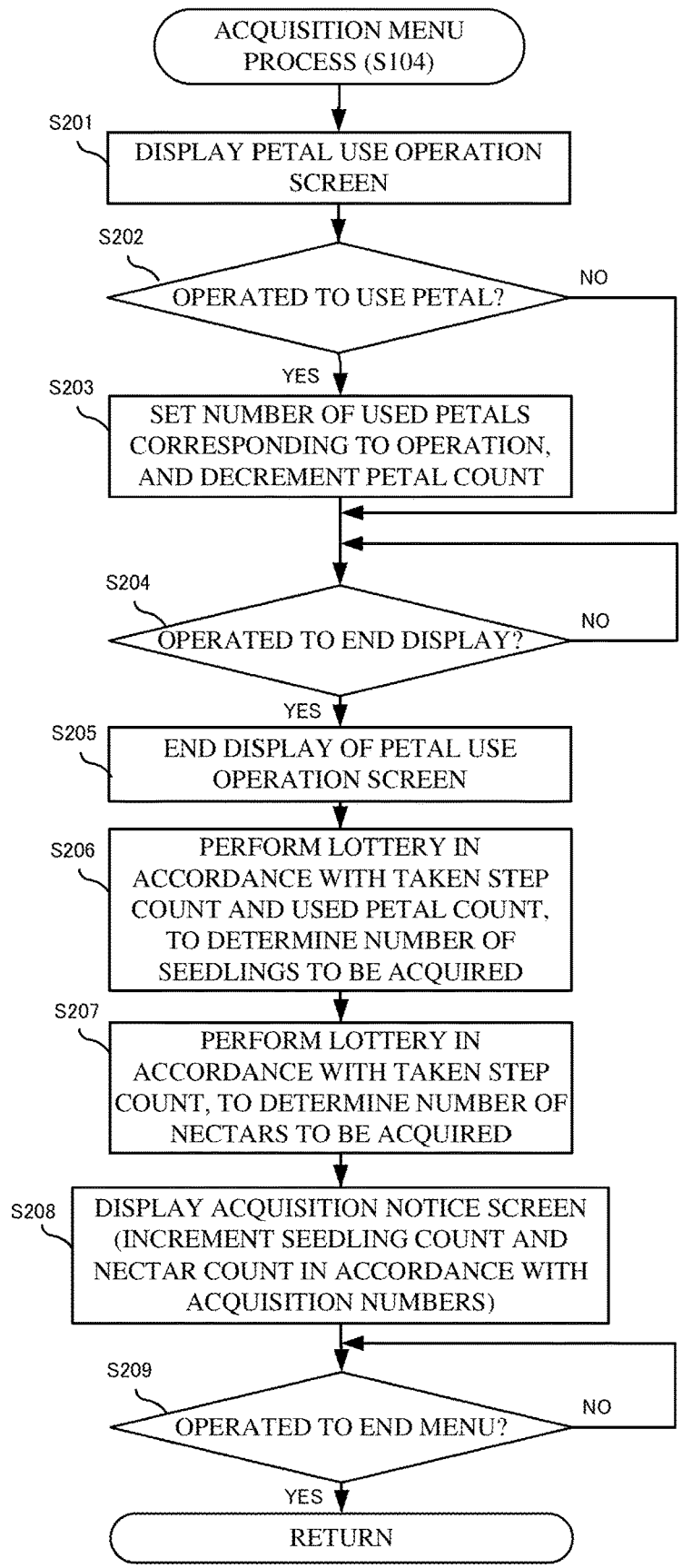
FIG. 14 is a non-limiting example of a flowchart showing the details of an acquisition menu process in FIG. 13.

FIG. 14 is an example of a flowchart showing the details of the acquisition menu process in step S104 in FIG. 13.

In step S201 in FIG. 14, the processor 11 displays the petal use operation screen described in FIG. 3(1), on the display section 15. Then, the process proceeds to step S202.

In step S202, the processor 11 determines whether or not petal use operation has been performed on the basis of the operation data 101 (see FIG. 12). Specifically, the processor 11 determines whether or not the petal use image 20 is tapped as described in FIG. 3(1). In the case of YES in this determination, the process proceeds to step S203, and in the case of NO in this determination, the process proceeds to step S204.

In step S203, the processor 11 sets the number of used petals corresponding to the number of times the user has performed petal use operation, on the basis of the operation data 101, and performs display of decrementing the number of petals. Specifically, as described in FIG. 3(1), in accordance with the number of times the petal use image 20 has been tapped, the processor 11 decrements the number of possessed petals indicated by the petal count data 122, and decrements the numbers of possessed petals displayed on the petal use image 20 and the petal count image 22. Then, the process proceeds to step S204.

In step S204, on the basis of the operation data 101, the processor 11 waits (NO) until operation of ending display of the petal use operation screen (tap operation on the word image 21 written as "NEXT" described in FIG. 3(1)) is performed, and if the display ending operation is performed (YES), the process proceeds to step S205.

In step S205, the processor 11 ends display of the petal use operation screen. Then, the process proceeds to step S206.

In step S206, the processor 11 performs a lottery in accordance with the number of taken steps and the number of used petals, to determine the number of seedlings to be acquired. Specifically, the processor 11 performs such a lottery that, the more the number of taken steps indicated by the second taken step count data 127 (the number of steps taken from the time when the acquisition notice screen shown in FIG. 3(2) was displayed last time) is, the more likely the number of acquired seedlings increases, and the more the number of used petals set in step S203 is, the more likely the number of acquired seedlings increases, thereby determining the number of seedlings to be acquired. The processor 11 adds the determined number of seedlings to the seedling count data 123. Then, the process proceeds to step S207.

In step S207, the processor 11 performs a lottery in accordance with the number of taken steps, to determine the number of nectars to be acquired. Specifically, the processor 11 performs such a lottery that, the more the number of taken steps indicated by the second taken step count data 127 (the number of steps taken from the time when the acquisition notice screen shown in FIG. 3(2) was displayed last time) is, the more likely the number of acquired nectars increases, thereby determining the number of nectars to be acquired. The processor 11 adds the determined number of nectars to the nectar count data 124. Then, the process proceeds to step S208.

In step S208, the processor 11 displays, on the display section 15, the acquisition notice screen for notifying the user about the numbers of seedlings and nectars acquired in step S206 and S207 as described in FIG. 3(2). Along with this, the processor 11 updates indication of the number of possessed seedlings on the seedling count image 23 and indication of the number of nectars on the nectar count image 24, on the basis of the seedling count data 123 and the nectar count data 124. Then, the process proceeds to step S209.

In step S209, the processor 11 waits (NO) until menu ending operation is performed, and if menu ending operation is performed (YES), ends the acquisition menu process and shifts the process to step S105 in FIG. 13. It is noted that the menu ending operation is operation of tapping a part where words "END MENU" (not shown) are displayed on the acquisition notice screen shown in FIG. 3(2), for example.

[Planter Menu Process]

Figure 15:
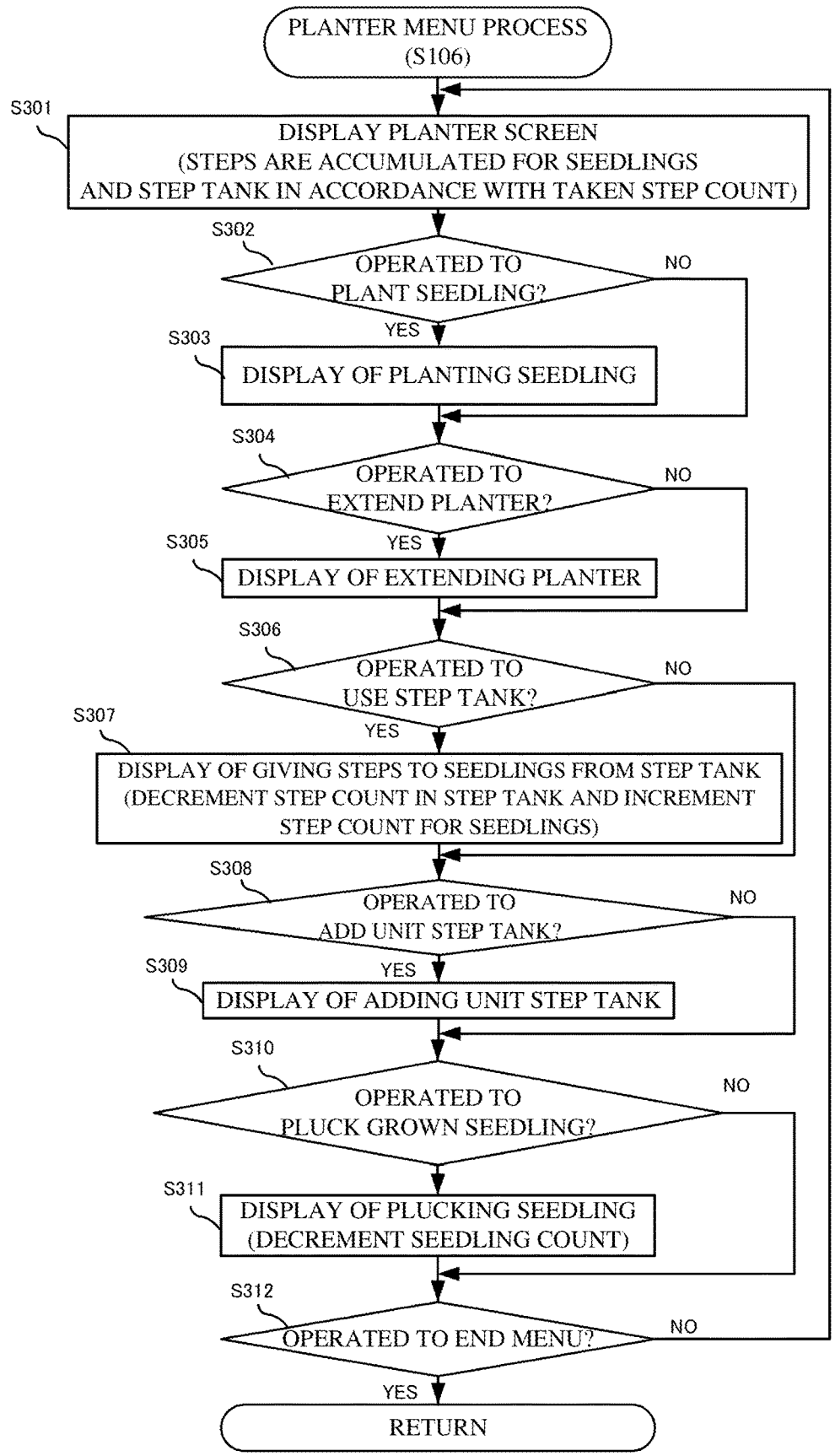
FIG. 15 is a non-limiting example of a flowchart showing the details of a planter menu process in FIG. 13.

FIG. 15 is an example of a flowchart showing the details of the planter menu process in step S106 in FIG. 13.

In step S301 in FIG. 15, the processor 11 displays the planter screen described in FIG. 4 to FIG. 7, on the display section 15. Specifically, the processor 11 adds the number of taken steps indicated by the third taken step count data 128 (see FIG. 12) (number of steps taken from the time when the planter screen was displayed last time), to the number of accumulated steps in the seedling data 105 for each seedling planted in the planter 30 (without exceeding the number of steps that can be accumulated), and also adds the same number of steps to the numbers of accumulated steps on the seedling accumulated step count images (33a, etc.) for the respective seedlings as described in FIG. 5. In addition, the processor 11 adds the number of taken steps indicated by the third taken step count data 128, to the number of accumulated steps in the step tank data 126 (without exceeding the number of steps that can be accumulated in accordance with the number of unit step tanks), and also adds the same number of steps to the number of accumulated steps in the step tank (step tank image 35) as described in FIG. 5. Then, the process proceeds to step S302.

In step S302, the processor 11 determines whether or not seedling planting operation has been performed, on the basis of the operation data 101. Specifically, the processor 11 determines whether or not seedling planting operation of tapping the seedling count image 23 has been performed as described in FIG. 4. In the case of YES in this determination, the process proceeds to step S303, and in the case of NO in this determination, the process proceeds to step S304.

In step S303, the processor 11 performs display of planting a seedling in the planter 30. Specifically, as described in FIG. 4, the processor 11 decrements the number of the seedling plantable parts 31 and increments the number of seedlings planted in the seedling plantable parts, which are indicated by the planter data 125, and performs display of planting a seedling in the seedling plantable part 31 of the planter 30. In addition, the processor 11 increments the number of seedlings planted in the planter 30, displayed on the seedling count image 23. Then, the process proceeds to step S304.

In step S304, the processor 11 determines whether or not planter extending operation described in FIG. 4 has been performed, on the basis of the operation data 101. In the case of YES in this determination, the process proceeds to step S305, and in the case of NO in this determination, the process proceeds to step S306.

In step S305, the processor 11 performs display of increasing the seedling plantable parts 31 of the planter 30. Specifically, as described in FIG. 4, the processor 11 increases the number of seedling plantable parts 31 indicated by the planter data 125 (without exceeding the extendable number), and performs display of increasing the seedling plantable parts 31 of the planter 30. In addition, the processor 11 updates the planter data 125 accordingly. Then, the process proceeds to step S306.

In step S306, the processor 11 determines whether or not step tank use operation has been performed for the unit step tank that has reached the upper limit accumulated step count 1000 as described in FIG. 6, on the basis of the operation data 101. In the case of YES in this determination, the process proceeds to step S307, and in the case of NO in this determination, the process proceeds to step S308.

In step S307, the processor 11 performs display of giving steps to each seedling from the step tank. Specifically, as described in FIG. 6, the processor 11 decrements the number of accumulated steps indicated by the step tank data 126, by 1000, and decrements the number of unit step tanks by 1, and also deletes the display of the unit step tank for which the step tank use operation has been performed. In addition, as described in FIG. 6, the processor 11 performs display of images 40 and increments, by 1000, the number of accumulated steps displayed on the seedling accumulated step count image 33 corresponding to each seedling planted in the planter 30 (without exceeding the number of steps that can be accumulated). Then, the process proceeds to step S308.

In step S308, the processor 11 determines whether or not unit step tank increasing operation described in FIG. 4 has been performed, on the basis of the operation data 101. It is noted that the unit step tank increasing operation cannot be performed if the number of unit step tanks has reached the upper limit number 5. In the case of YES in this determination, the process proceeds to step S309, and in the case of NO in this determination, the process proceeds to step S310.

In step S309, the processor 11 performs display of incrementing the number of unit step tanks. Specifically, as described in FIG. 4, the processor 11 increments the number of unit step tanks indicated by the step tank data 126, and performs display of adding a unit step tank on which 0 is indicated as the number of accumulated steps. Then, the process proceeds to step S310.

In step S310, the processor 11 determines whether or not plucking operation for a seedling the growth of which is finished has been performed as described in FIG. 7, on the basis of the operation data 101. In the case of YES in this determination, the process proceeds to step S311, and in the case of NO in this determination, the process proceeds to step S312.

In step S311, the processor 11 performs display of plucking the grown seedling. Specifically, the processor 11 changes the state indicated by the character state data 104 corresponding to the seedling to be plucked, from the state of the seedling planted in the planter 30 to a double-leaf state, and resets the number of accumulated steps, etc. indicated by the seedling data 105 to 0. Also, the processor 11 decrements the number of possessed seedlings indicated by the seedling count data 123 by 1, increments the number of seedling plantable parts 31 indicated by the planter data 125 by 1, and decrements the number of seedlings planted in the seedling plantable parts 31 by 1. In addition, as described in FIG. 7, the processor 11 performs display of plucking the grown seedling, and decrements the number of possessed seedlings, etc. displayed on the seedling count image 23. Then, the process proceeds to step S312.

In step S312, the processor 11 determines whether or not menu ending operation has been performed. In the case of YES in this determination, the planter menu process is ended and the process proceeds to step S107 in FIG. 13, and in the case of NO in this determination, the process returns to step S301, to continue displaying the planter screen. It is noted that the menu ending operation is operation of tapping a part where words "END MENU" (not shown) are displayed on the planter screen shown in FIG. 4, etc., for example.

[Character Menu Process]

Figure 16:
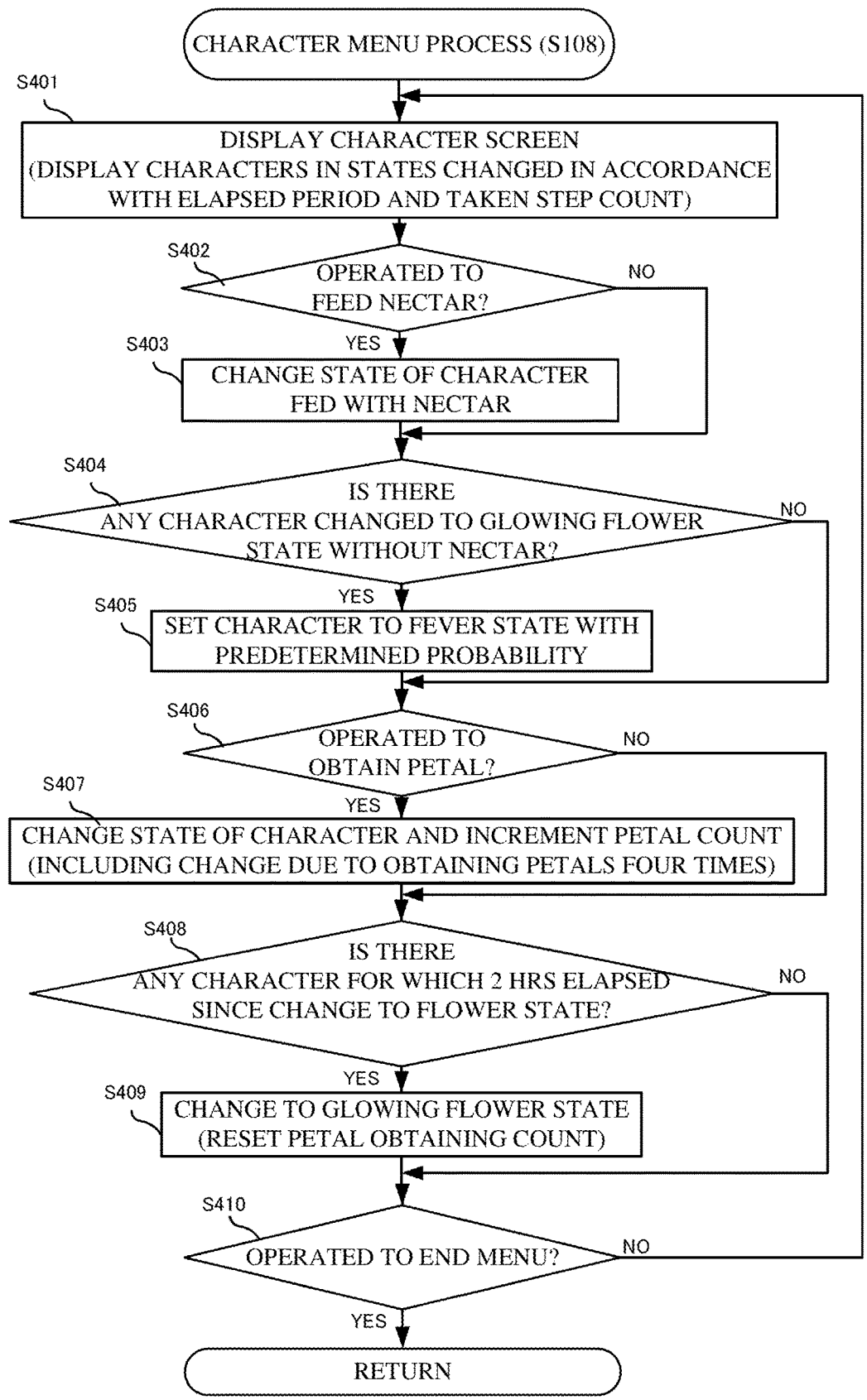
FIG. 16 is a non-limiting example of a flowchart showing the details of a character menu process in FIG. 13.

FIG. 16 is an example of a flowchart showing the details of the character menu process in step S108 in FIG. 13.

In step S401 in FIG. 16, the processor 11 displays, on the display section 15, a character screen on which the characters 40 in states based on the elapsed periods, the number of taken steps, etc., are displayed as described in FIG. 8 to FIG. 11. Specifically, the processor 11 calculates the state of each character 40 on the basis of the condition of the character displayed last time, indicated by the last-time character condition data 106, and the time history of the number of taken steps indicated by the first taken step count data 107 (see FIG. 12), and performs display of the respective characters 40 in the calculated states. In addition, in a case where the present time is past 4:00 at which the character 40 should be reset to a double-leaf state, the processor 11 calculates the state of each character 40, considering the elapsed period since 4:00, and performs display of each character 40 in the calculated state. In addition, the processor 11 prohibits the character 40e in a leafless state from changing to a double-leaf state during a time period from 0:00 to 4:00, and considering this, calculates the states of the characters 40 and performs display of the respective characters 40 in the calculated states. Then, in accordance with the changed states, the processor 11 updates the character state data 104. The character screen is displayed as described above, whereby the characters 40 are displayed in states changed in accordance with the elapsed period, the number of taken steps, etc., as described in FIG. 11. Then, the process proceeds to step S402.

In step S402, the processor 11 determines whether or not nectar feeding operation described in FIG. 9 has been performed, on the basis of the operation data 101. Here, as described in FIG. 9, nectar feeding operation can be performed for only a specific character 40. In the case of YES in this determination, the process proceeds to step S403, and in the case of NO in this determination, the process proceeds to step S404.

In step S403, the processor 11 performs display of feeding nectar to the character 40 and changing the state thereof. Specifically, as described in FIG. 9, the processor 11 decrements the number of possessed nectars indicated by the nectar count data 124, and performs display of changing the state of the character 40 fed with nectar. In addition, the processor 11 updates the nectar growth data 108 and decrements the number of nectars displayed on the nectar count image 24. Then, in accordance with the changed state, the processor 11 updates the character state data 104. Then, the process proceeds to step S404.

In step S404, the processor 11 determines whether or not there is a character 40 that has changed to a glowing flower state without being fed with nectar, on the basis of the nectar growth data 108 for each character 40. In the case of YES in this determination, the process proceeds to step S405, and in the case of NO in this determination, the process proceeds to step S406.

In step S405, for the character 40 that has changed to a glowing flower state without being fed with nectar, the processor 11 performs a lottery having a predetermined winning probability (e.g., 10%). In a case of winning in the lottery, the processor 11 sets a fever state as described in FIG. 11. In this case, on the basis of the fever data 110, for the character 40c in the glowing flower state set in the fever state, the processor 11 performs processing of repeating, up to three times, such a loop that a petal is obtained and the character state changes to a flower state and returns to a glowing flower state in three seconds after that. Then, the process proceeds to step S406.

In step S406, for the character 40c in the glowing flower state, the processor 11 determines whether or not petal obtaining operation described in FIG. 10 has been performed, on the basis of the operation data 101. In the case of YES in this determination, the process proceeds to step S407, and in the case of NO in this determination, the process proceeds to step S408.

In step S407, the processor 11 changes the state of the character 40c in a glowing flower state for which petal obtaining operation has been performed, and increments the number of possessed petals. Specifically, the processor 11 increments the petal obtaining count (the number of times of petal obtaining operation) indicated by the petal obtaining count data 109, by 1. Then, if the incremented petal obtaining count is 1 to 3, the processor 11 performs display of changing the character 40c in a glowing flower state to a flower state, and if the incremented petal obtaining count is 4, the processor 11 performs display of changing the character 40c in a glowing flower state to a leafless state. Here, on the basis of the petal obtaining count data 109, in a case of obtaining a petal for the first time after the character 40 has come into a glowing flower state, the processor 11 increments the number of possessed petals indicated by the petal count data 122, by 2, and increments the number of possessed petals displayed on the petal count image 22, by 2. In a case of obtaining a petal for the second or subsequent time after the character 40 has come into a glowing flower state, the processor 11 increments the number of possessed petals indicated by the petal count data 122, by 1, and increments the number of possessed petals displayed on the petal count image 35, by 1. Then, in accordance with the changed state, the processor 11 updates the character state data 104. Then, the process proceeds to step S408.

In step S408, the processor 11 determines whether or not there is a character 40d for which two hours have elapsed since the character has changed to a flower state, on the basis of the time data 121. In the case of YES in this determination, the process proceeds to step S409, and in the case of NO in this determination, the process proceeds to step S410.

In step S409, the processor 11 changes the character 40d in a flower state determined in step S408, to a glowing flower state. In addition, the processor 11 resets the petal obtaining count indicated by the petal obtaining count data 109, to 0. Then, in accordance with the changed state, the processor 11 updates the character state data 104. Then, the process proceeds to step S410.

In step S410, the processor 11 determines whether or not menu ending operation has been performed. In the case of YES in this determination, the character menu process is ended and the process proceeds to step S109 in FIG. 13, and in the case of NO in this determination, the process returns to step S401, to continue displaying the character screen. It is noted that the menu ending operation is operation of tapping a part where words "END MENU" (not shown) are displayed on the character screen shown in FIG. 8, etc., for example.

It is noted that seedlings, characters, etc., displayed on the display screens described with reference to FIG. 2 to FIG. 11, etc., may be referred to as "in-game objects". In addition, a seedling planted in the planter 30 may be referred to as "active object". In addition, a petal that can be obtained in this game may be referred to as "in-game reward". In addition, the number of steps taken through the user walking (or running) and the numbers of steps accumulated for seedlings and the step tank may be referred to as "parameters" regarding the exercise amount. In addition, nectar may be referred to as "state change item".

As described above, in the exemplary embodiment, the user takes steps through walking (or running), thereby raising the probability of acquiring seedlings, accumulates steps for seedlings and the step tank, grows the seedlings, and increasingly acquires the characters 40, thus enjoying the game. In addition, by taking steps through walking (or running), the user changes (grows) the character 40 to increase the number of petals to be obtained, and uses the petals to raise the probability of acquiring seedlings, and as a result, the number of acquired characters 40 is further increased and thus the user can enjoy the game. With such features, the exemplary embodiment can provide the user with a motivation to walk (or run), i.e., exercise.

In the exemplary embodiment, by taking steps, it is possible to acquire seedlings and nectars, grow the seedlings, and change (grow) the characters 40 simultaneously (in parallel). Thus, the exemplary embodiment can provide the user with a motivation to exercise.

In the exemplary embodiment, even after the character 40 has grown into a glowing flower state in which a petal can be obtained, the character 40 returns to a leafless state or a double-leaf state if a petal is obtained a predetermined number of times or a specific time (4:00) has arrived (see FIG. 11). Thus, the exemplary embodiment enables the user to keep motivated to continue exercise.

In the exemplary embodiment, steps are accumulated for both of seedlings planted in the planter 30 and the step tank, and even if the number of accumulated steps for the planted seedling has reached the upper limit and thus steps are not accumulated for that seedling any longer, steps are accumulated in the step tank from which the steps can be given to seedlings. Thus, in the exemplary embodiment, even if the number of accumulated steps for the planted seedling has reached the upper limit, the user can keep motivated to continue exercise.

[Modifications]

The above exemplary embodiment has shown the example in which the character 40 can change from a double-leaf state to a bud state in accordance with the elapsed period or taken steps (see FIG. 11). However, control may be performed such that the character 40 can change from a double-leaf state to a bud state only by being fed with nectar.

The above exemplary embodiment has shown the example in which the character 40 can change from a bud state to a glowing flower state in accordance with the elapsed period or taken steps (see FIG. 11). However, control may be performed such that the character 40 can change from a bud state to a glowing flower state only by being fed with nectar.

The above exemplary embodiment has shown the example in which the character 40 can change from a flower state to a glowing flower state in accordance with the elapsed period (see FIG. 11). However, control may be performed such that the character 40 can change from a flower state to a glowing flower state only by being fed with nectar.

The above exemplary embodiment has shown the example in which the character 40 immediately changes from a double-leaf state to a bud state by being fed with nectar and immediately changes from a bud state to a glowing flower state by being fed with nectar (see FIG. 11). However, control may be performed such that the character 40 immediately changes from a double-leaf state to a glowing flower state by being fed with special nectar (special nectar different from normal nectar described in FIG. 3(2), FIG. 9, FIG. 11, etc.). That is, control may be performed so as to provide special nectar that allows the character 40 in a double-leaf state to change to a glowing flower state without experiencing a bud state. In the case of performing such control, if the special nectar is fed to the character 40 in a bud state, the character 40 may immediately change from a bud state to a glowing flower state (as in the case of feeding normal nectar). For the special nectar, a display manner such as color may be set to be different from that for normal nectar, and for example, control may be performed such that the special nectar is acquired through a lottery as in the case of normal nectar (see S207 in FIG. 14) and then is displayed on the acquisition screen described in FIG. 3(2), etc.

The above exemplary embodiment has shown the example in which the character 40 that has changed from a double-leaf state to a glowing flower state without being fed with nectar is set to a fever state with a predetermined probability (see S404, S405 in FIG. 16). However, for example, control may be performed such that the character 40 that has grown by being fed with special nectar (special nectar different from normal nectar described in FIG. 3(2), FIG. 9, FIG. 11, etc.) at least once in a process of changing from a double-leaf state to a glowing flower state is necessarily set to a fever state when changing to a glowing flower state, irrespective of whether or not normal nectar has been fed. That is, control may be performed so as to provide special nectar with which the character 40 necessarily comes into a fever state when changing to a glowing flower state. Alternatively, for example, control may be performed such that the character 40 that has grown by being fed with special nectar at least once in a process of changing from a double-leaf state to a glowing flower state is necessarily set to a fever state when changing to a glowing flower state, on the condition that normal nectar has not been fed. For the special nectar, a display manner such as color may be set to be different from that for normal nectar, and for example, control may be performed such that the special nectar is acquired through a lottery as in the case of normal nectar (see S207 in FIG. 14) and then is displayed on the acquisition screen described in FIG. 3(2), etc.

The above exemplary embodiment has shown the example in which the number of kinds of a flower to bloom on the character 40 in a glowing flower state (or flower state) is one (see FIG. 10 and FIG. 11). However, for example, control may be performed such that a special kind of flower blooms on the character 40 that has grown by being fed with special nectar (special nectar different from normal nectar described in FIG. 3(2), FIG. 9, FIG. 11, etc.) at least once in a process of changing from a double-leaf state to a glowing flower state. That is, control may be performed so as to provide special nectar that allows a special kind of flower to bloom. For the special nectar, a display manner such as color may be set to be different from that for normal nectar, and for example, control may be performed such that the special nectar is acquired through a lottery as in the case of normal nectar (see S207 in FIG. 14) and then is displayed on the acquisition screen described in FIG. 3(2), etc.

The above exemplary embodiment has shown the example in which the character 40 changes from a double-leaf state to a bud state when a fixed period (eight hours) has elapsed (in a case where there are no steps taken) (see FIG. 11). However, control may be performed such that the character 40 can change from a double-leaf state to a bud state when a period (e.g., random period) determined in a predetermined range (e.g., range of 8 to 16 hours) in accordance with a lottery or the like has elapsed (in a case where there are no steps taken).

The above exemplary embodiment has shown the example in which the character 40 changes from a bud state to a glowing flower state when a fixed period (eight hours) has elapsed (in a case where there are no steps taken) (see FIG. 11). However, control may be performed such that the character 40 can change from a bud state to a glowing flower state when a period (e.g., random period) determined in a predetermined range (e.g., range of 8 to 16 hours) in accordance with a lottery or the like has elapsed (in a case where there are no steps taken).

The above exemplary embodiment has shown the example in which the character 40 changes from a flower state to a glowing flower state when a fixed period (two hours) has elapsed (see FIG. 11). However, control may be performed such that the character 40 can change from a flower state to a glowing flower state when a period (e.g., random period) determined in a predetermined range (e.g., range of 1 to 3 hours) in accordance with a lottery or the like has elapsed.

The above exemplary embodiment has shown the example in which the character 40 changes from a leafless state to a double-leaf state when a fixed period (six hours) has elapsed (in a case other than a time period in which the character state cannot change and where there are no steps taken) (see FIG. 11). However, control may be performed such that the character 40 can change from a leafless state to a double-leaf state with a required number of (taken) steps (e.g., a random number of steps) determined in a predetermined range (e.g., range of 500 to 1000 steps) in accordance with a lottery or the like (in a case other than a time period in which the character state cannot change and where there are no steps taken).

In the above exemplary embodiment (see FIG. 11), control may be performed such that, in a case where the character 40 is grown by being fed with nectar and comes into a glowing flower state, the number of times a petal can be obtained after the character 40 has come into a glowing flower state becomes smaller (e.g., by two) than in a case where the character 40 is grown without being fed with nectar and comes into a glowing flower state.

In the above exemplary embodiment (see FIG. 11), control may be performed such that, in some cases, the character 40 returns to a seedling state (see FIG. 3(2)). In this case, control may be performed such that the probability for the character 40 to return to a seedling state increases as the number of times the character 40 has come into a leafless state by a petal being obtained (picked) therefrom increases. For example, control may be performed such that the probability for the character 40 to return to a seedling state increases by 10% per one-count increase in the number of times the character 40 has come into a leafless state. In this case, control may be performed such that, if the number of times the character 40 has come into a leafless state by a petal being obtained therefrom has reached a predetermined number of times (e.g., five times), the character 40 returns to a seedling state (at a next timing of coming into a leafless state, for example). Further, control may be performed such that the seedling (character in a seedling state) to which the character 40 has returned can be returned to the character 40*a* in a double-leaf state, using steps (e.g., 100 steps) taken through walking or the like of the user or using the steps (e.g., 100 steps) accumulated in the step tank. In addition, control may be performed such that the seedling (character in a seedling state) to which the character 40 has returned returns to the character 40*a* in a double-leaf state (automatically without user's operation or in accordance with user's operation) on the basis of a specific time having arrived (e.g., 4:00). Alternatively, control may be performed such that the character 40 does not change to a double-leaf state (is prohibited from changing to a double-leaf state) even in a case of a specific time (e.g., 4:00) having arrived.

The above exemplary embodiment has shown the example in which steps taken by the user walking (or running) are accumulated for both of seedlings and the step tank simultaneously (in parallel), and steps can be accumulated in the step tank even after the seedling has reached the upper limit number of accumulated steps (e.g., 1000 steps). However, for example, control may be performed such that, firstly, steps taken by the user walking (or running) are preferentially accumulated for seedlings, and only after all the seedlings planted in the planter have reached the upper limit number of accumulated steps (e.g., 1000 steps or 3000 steps; see FIG. 5), steps can be accumulated in the step tank.

The above exemplary embodiment has shown the example in which the accumulated steps in the step tank 35 are used on a 1000-step basis (see FIG. 6). However, for example, control may be performed such that steps are given to the seedling by an amount corresponding to a period during which the user is touching the step tank 35 (unit step tank 35*a*, etc.). For example, 100 steps may be given to the seedling when the user has touched for one second.

The above exemplary embodiment has shown the example in which a petal can be obtained by performing petal obtaining operation on the character 40 (see FIG. 10, FIGS. 11, S406 and S407 in FIG. 16). However, for example, a parameter indicating a friendship level may be set for each character 40, and control may be performed such that, by performing petal obtaining operation on the character 40, a petal can be obtained and the parameter indicating the friendship level of the character 40 is increased. That is, control may be performed such that, as petals are more obtained, the friendship level of the character 40 from which the petals have been obtained increases, so that the user can become friendly with the character 40.

The above exemplary embodiment has shown the example in which, for the character image 40*c* in a glowing flower state that has come into a fever state, the fever state is canceled after three-time repetition of such a loop that a petal is obtained and the character state changes to a flower state and returns to a glowing flower state in three seconds after that (see FIG. 11). However, for example, control may be performed such that, for the character image 40*c* in a glowing flower state that has come into a fever state, the fever state is canceled after petals are obtained in accordance with the number of times the user has performed tap operation during a predetermined period (e.g., five seconds) from the first tap operation by the user. For example, in response to the user first tapping the character image 40c in a glowing flower state that has come into a fever state, two petals (or, for example, one petal) are obtained and also a period of five seconds during which petals can be obtained is started. Then, petals are obtained one by one in accordance with the number of times of tap operation performed during the five seconds, and thus the fever state is canceled. Alternatively, for example, in response to the user first tapping the character image 40c in a glowing flower state that has come into a fever state, a period of five seconds during which petals can be obtained is started (i.e., no petals are obtained with this first tap operation). Then, petals are obtained one by one in accordance with the number of times of tap operation performed during the five seconds, and thus the fever state is canceled.

The above exemplary embodiment has shown the example in which change of the character 40 is hastened (the period until change is shortened) by steps taken by the user (see FIG. 11). However, control may be performed such that change of the character 40 is hastened through exercise without using steps. In this case, the detection section 16 is a device for measuring an exercise amount of the user, and is, for example, a device for measuring the number of heartbeats (number of pulses), the number of breaths, the respiratory volume, etc. per unit period, of the user. In addition, for example, control may be performed such that the period (six hours) needed for change from a leafless state to a double-leaf state is shortened using steps, and the period (eight hours) needed for change from a double-leaf state to a bud state, or the like, is shortened using the number of heartbeats, etc., as described above.

The above exemplary embodiment has shown the example in which, while the planter screen is displayed or the character screen is displayed, calculation is performed for reflecting the number of taken steps, the elapsed period, and the like in the states of objects (seedlings, step tank, characters), and the resultant screen is displayed (see S301 in FIG. 15, S401 in FIG. 16, etc.). However, for example, control may be performed such that, even when the application of this game is not being activated, a part of the application function of this game is exerted to constantly (in real time) calculate the states of objects (seedlings, step tank, characters) on the basis of the number of taken steps, the elapsed period, and the like, and then, when the planter screen is displayed or the character screen is displayed, the objects are displayed in the calculated states.

The above exemplary embodiment has shown the example in which a series of processing steps in the game process is executed by a single apparatus. However, the above series of processing steps may be executed by an information processing system including a plurality of information processing apparatuses. For example, in an information processing system including a terminal-side apparatus and a server-side apparatus capable of communicating with the terminal-side apparatus via a network, a part of the above series of processing steps may be executed by the server-side apparatus. Further, in an information processing system including a terminal-side apparatus and a server-side apparatus capable of communicating with the terminal-side apparatus via a network, major processing of the above series of processing steps may be executed by the server-side apparatus, and a part of the above series of processing steps may be executed by the terminal-side apparatus. In addition, in the above information processing system, a server-side system may be composed of a plurality of information processing apparatuses and processing to be executed on the server side may be executed by the plurality of information processing apparatuses in a shared manner.

While the exemplary embodiments have been described herein, it is to be understood that the above description is, in all aspects, merely an illustrative example, and is not intended to limit the scope thereof. It is to be understood that various modifications and variations can be made without deviating from the scope of the exemplary embodiments.

What is claimed is:

1. A non-transitory computer-readable storage medium having stored therein instructions that, when executed by a processor of an information processing apparatus, cause the information processing apparatus to perform operations comprising:
    associating a first parameter with each of a plurality of in-game objects independently;
    setting the in-game object the number of which is not more than a first upper limit among the plurality of in-game objects, as an active object;
    incrementing only the first parameter associated with the active object, in accordance with an exercise amount of a user;
    in accordance with the exercise amount of the user, incrementing a second parameter even when the first parameter has not reached a second upper limit, and incrementing the second parameter also when the first parameter has reached the second upper limit; and
    incrementing the first parameter based on decrementing the second parameter; and
    giving the user an in-game reward according to the active object with which the first parameter is associated, when the first parameter has reached the second upper limit.

2. The non-transitory computer-readable storage medium according to claim 1, wherein an amount by which the second parameter is incremented in accordance with the exercise amount of the user, is not made different between a case where the first parameter has reached the second upper limit and a case where the first parameter has not reached the second upper limit.

3. The non-transitory computer-readable storage medium according to claim 1, wherein the instructions, when executed, cause the information processing apparatus to perform further operations comprising making amounts by which the first parameter and the second parameter are incremented in accordance with the exercise amount of the user, equal between the first parameter and the second parameter.

4. The non-transitory computer-readable storage medium according to claim 1, wherein in a case where there are a plurality of the active objects, an amount by which the first parameter associated with each of the plurality of active objects is incremented in accordance with the exercise amount of the user is not changed depending on a number of the active objects.

5. The non-transitory computer-readable storage medium according to claim 4, wherein an amount by which the first parameter associated with each of the active objects is incremented based on decrementing the second parameter is not changed depending on the number of the active objects.

6. The non-transitory computer-readable storage medium according to claim 1, wherein in a case of decrementing the second parameter, the decrement is a natural number multiple of a decrement unit.

7. The non-transitory computer-readable storage medium according to claim 6, wherein:
the second parameter is not incremented in a case where the second parameter has reached a third upper limit, and
every time the second parameter is decremented by the natural number multiple of the decrement unit, the third upper limit is lowered by an amount corresponding to the natural number.

8. The non-transitory computer-readable storage medium according to claim 1, wherein the first parameter is not incremented in a case where the first parameter has reached the second upper limit.

9. The non-transitory computer-readable storage medium according to claim 1, wherein the active object is prohibited from changing to another in-game object different from that active object until the first parameter associated with the active object reaches the second upper limit.

10. A game processing system, comprising:
a processor and a memory coupled thereto, the processor being configured to control the game processing system to at least:
associate a first parameter with each of a plurality of in-game objects independently;
set the in-game object the number of which is not more than a first upper limit among the plurality of in-game objects, as an active object;
increment only the first parameter associated with the active object, in accordance with an exercise amount of a user;
in accordance with the exercise amount of the user, increment a second parameter even when the first parameter has not reached a second upper limit, and increment the second parameter also when the first parameter has reached the second upper limit; and
increment the first parameter based on decrementing the second parameter; and
give the user an in-game reward according to the active object with which the first parameter is associated, when the first parameter has reached the second upper limit.

11. A game processing method performed using a game processing system comprising a processor, the game processing method comprising:
associating a first parameter with each of a plurality of in-game objects independently;
setting the in-game object the number of which is not more than a first upper limit among the plurality of in-game objects, as an active object;
incrementing only the first parameter associated with the active object, in accordance with an exercise amount of a user;
in accordance with the exercise amount of the user, incrementing a second parameter even when the first parameter has not reached a second upper limit, and incrementing the second parameter also when the first parameter has reached the second upper limit; and
incrementing the first parameter based on decrementing the second parameter; and
giving the user an in-game reward according to the active object with which the first parameter is associated, when the first parameter has reached the second upper limit.

12. A game processing apparatus, comprising:
a processor and a memory coupled thereto, the processor being configured to control the game processing apparatus to at least:
associate a first parameter with each of a plurality of in-game objects independently;
set the in-game object the number of which is not more than a first upper limit among the plurality of in-game objects, as an active object;
increment only the first parameter associated with the active object, in accordance with an exercise amount of a user;
in accordance with the exercise amount of the user, increment a second parameter even when the first parameter has not reached a second upper limit, and increment the second parameter also when the first parameter has reached the second upper limit; and
increment the first parameter based on decrementing the second parameter; and
give the user an in-game reward according to the active object with which the first parameter is associated, when the first parameter has reached the second upper limit.

13. The method according to claim 11, wherein an amount by which the second parameter is incremented in accordance with the exercise amount of the user, is not made different between a case where the first parameter has reached the second upper limit and a case where the first parameter has not reached the second upper limit.

14. The method according to claim 11, further comprising making amounts by which the first parameter and the second parameter are incremented in accordance with the exercise amount of the user, equal between the first parameter and the second parameter.

15. The method according to claim 11, wherein in a case where there are a plurality of the active objects, an amount by which the first parameter associated with each of the plurality of active objects is incremented in accordance with the exercise amount of the user is not changed depending on a number of the active objects.

16. The method according to claim 15, wherein an amount by which the first parameter associated with each of the active objects is incremented based on decrementing the second parameter is not changed depending on the number of the active objects.

17. The method according to claim 11, wherein in a case of decrementing the second parameter, the decrement is a natural number multiple of a decrement unit.

18. The method according to claim 17, wherein:
the second parameter is not incremented in a case where the second parameter has reached a third upper limit, and
every time the second parameter is decremented by the natural number multiple of the decrement unit, the third upper limit is lowered by an amount corresponding to the natural number.

19. The method according to claim 11, wherein the first parameter is not incremented in a case where the first parameter has reached the second upper limit.

20. The method according to claim 11, wherein the active object is prohibited from changing to another in-game object different from that active object until the first parameter associated with the active object reaches the second upper limit.

* * * * *